United States Patent
Olson et al.

(10) Patent No.: US 7,439,231 B2
(45) Date of Patent: Oct. 21, 2008

(54) INHIBITORS OF ANTIGEN PRESENTATION BY MHC CLASS II MOLECULES AND METHODS OF USE THEREOF

(75) Inventors: Gary Olson, Mountainside, NJ (US); Charles Cook, Mendham, NJ (US); Christopher Self, West Caldwell, NJ (US)

(73) Assignee: Provid Pharmaceuticals, Inc., North Brunswick, NJ (US)

( * ) Notice: Subject to any disclaimer, the term of this patent is extended or adjusted under 35 U.S.C. 154(b) by 594 days.

(21) Appl. No.: 10/778,756

(22) Filed: Feb. 13, 2004

(65) Prior Publication Data

US 2004/0162242 A1    Aug. 19, 2004

Related U.S. Application Data

(60) Provisional application No. 60/447,949, filed on Feb. 14, 2003.

(51) Int. Cl.
*A61K 38/08* (2006.01)

(52) U.S. Cl. .............................. 514/17; 514/18; 53/329; 53/330

(58) Field of Classification Search ........................ None
See application file for complete search history.

(56) References Cited

U.S. PATENT DOCUMENTS

| | | | |
|---|---|---|---|
| 4,224,316 A * | 9/1980 | Momany | 514/17 |
| 4,839,344 A * | 6/1989 | Bowers et al. | 514/16 |
| 5,624,902 A * | 4/1997 | Blondelle et al. | 514/17 |
| 5,817,629 A | 10/1998 | Warren et al. | |
| 5,858,980 A | 1/1999 | Weiner et al. | |
| 5,874,531 A | 2/1999 | Strominger et al. | |
| 6,207,644 B1 | 3/2001 | Luke et al. | |
| 6,355,617 B1 | 3/2002 | Luke et al. | |
| 2002/0133027 A1 | 9/2002 | Smith, III et al. | |

FOREIGN PATENT DOCUMENTS

| | | |
|---|---|---|
| WO | WO 94/20127 | 9/1994 |
| WO | WO 96/12731 | 5/1996 |
| WO | WO98/12212  * | 3/1998 |
| WO | WO 03/082197 A2 | 10/2003 |

OTHER PUBLICATIONS

Yoo, Sung-eun. 'Angiotensin II Receptor Antagonists for New Antihypertensives' Korean J. of Med. Chem. vol. 6, No. 2, pp. 325-328. 1996.*

Fiorenza et al., "Peptidomimetic compounds that inhibit antigen presentation by autoimmune disease-associated class II major histocompatibility molecules," Nature Biotechnology 17:562-567 (1999).

Lehmann et al., "Selective peptidomimetic blockers of autoantigen presentation: a novel therapeutic approach to autoimmune disease," Trends in Pharmacological Sciences (Elsevier, Haywarth, GB) 21(3):79-80.

Adorini, et al., (1988), "In Vivo Competition Between Self Peptides and Foreign Antigens in T-cell Activation", Nature, 334, 623-625.

Bolin, et al., (2000), "Peptide and Peptide Mimetic Inhibitors of Antigen Presentation by HLA-DR Class II MHC Molecules, Design, Structure-Activity Relationships, and X-ray Crystal Structures", J. Med. Chem., 43, 2135-2148.

Falcioni, et al., (1999), "Peptidomimetic compounds that inhibit antigen presentation by autoimmune disease-associated class II major histocompatibility molecules", Nature Biotechnology, 17, 562-567.

Giordano, M. et al. (2002), "Genetics of Multiple Sclerosis—Linkage and Association Studies", Am. J. Pharmacogenomics 2:37-58.

Hammer, J. et al. (1993), "Promiscuous and Allele-Specific Anchors in HLA-DR-Binding Peptides", Cell 74:197-203.

Ishioka, et al., (1994), "Failure to Demonstrate Long-Lived MHC Saturation Both In Vitro and In Vivo", J. Immunol. 152, 4310-4319.

Lamont, et al. (1990), "The Use of Peptide Analogs with Improved Stability and MHC Binding Capacity to Inhibit Antigen Presentation In Vitro and In Vivo", J. Immunol. 144, 2493-2498.

Smith et al. (1998), "Crystal Structure of HLA-DR2 (DRA*0101,DRB1*1501) Complexed with a Peptide from Human Myelin Basic Protein", J. Exp. Med. 188:1511-1520.

Stern et al. (1994), "Crystal Structure of the Human Class II MHC Protein HLA-DR1 Complexed with an Influenza Virus Peptide", Nature 368:215-221.

Wucherpfennig et al. (1994), "Structural Requirements for Binding of an Immunodominant Myelin Basic Protein Peptide to DR2 Isotypes and for Its Recognition by Human T Cell Clones", J. Exp. Med. 179:279-290.

Yusuf-Makagiansar et. al. (2002), "Inhibition of LFA-1/ICAM-1 and VLA-4/VCAM-1 as a Therapeutic Approach to Inflammation and Autoimmune Diseases", Med. Res. Rev. 22(2):146-167.

* cited by examiner

Primary Examiner—Anish Gupta
(74) Attorney, Agent, or Firm—Jones Day

(57) ABSTRACT

The present invention relates to compounds, pharmaceutical compositions containing such compounds and methods for their use. In particular, the compounds of the invention are useful for the treatment or prevention of diseases associated with T cell proliferation such as autoimmune diseases and disorders.

10 Claims, No Drawings

INHIBITORS OF ANTIGEN PRESENTATION BY MHC CLASS II MOLECULES AND METHODS OF USE THEREOF

This application claims the benefit of U.S. provisional application No. 60/447,949, filed Feb. 14, 2003, the contents of which are incorporated by reference herein in their entirety.

1. FIELD OF THE INVENTION

This invention relates to novel compounds, pharmaceutical compositions containing such compounds and methods for their use. In particular, the compounds of the invention are useful for the treatment or prevention of autoimmune diseases and disorders.

2. BACKGROUND OF THE INVENTION

2.1 Autoimmune Disorders

Host immune responses are commonly classified into two distinguishable groups, cellular and humoral. Cellular immunity is mediated by T lymphocytes or T cells and protects against virally infected cells, fungi, parasites, and foreign tissue. Humoral immunity, which is mediated by B lymphocytes or B cells through the production of antibodies, is most effective against bacterial infections and the extracellular phases of viral infections. D. Voet & J. Voet, *Biochemistry* 1208 (2d ed., Wiley 1995).

Cellular immune response cascades lead to the destruction of antigens through: 1) the uptake of antigens by cellular macrophages or antigen presenting cells, 2) the processing or fragmentation of the antigen within the macrophage, 3) the association of the fragmented antigen with cell-surface proteins known as the major histocompatibility complex ("MHC") proteins and 4) binding of the MHC protein/antigen complex by T cells that are induced to propagate, thereby illiciting an effective immune response against the specific antigen. In autoimmune disorders, this cellular immune response cascade recognizes self-derived species as antigens, effectively leading to the destruction of host peptides, cells, and tissues. The process by which the cellular immune system recognizes and initiates a response to antigens, both foreign and self, has been a focus of much research in recent years.

MHC proteins have been classified into two groups, referred to as Class I and Class II MHC proteins, that are structurally and functionally similar. D. Voet & J. Voet, Id. Macrophages exhibiting Class I MHC proteins or Class II MHC proteins that are complexed with an antigen on their surface are bound by cytotoxic T cells or helper T cells, respectively. As a result of this binding event, T cells are induced to proliferate and trigger an immune response against the antigen. The role of MHC proteins is to present the antigen on the surface of the cell so that they can be recognized by T cells. In humans, the Class I MHC proteins are encoded by three separate genetic loci, HLA-A, HLA-B, and HLA-C. There are also three heterodimeric human Class II MHC proteins whose alpha and beta chains are encoded by genes designated HLA-DP, HLA-DQ, and HLA-DR. Both Class I and Class II MHC genes are highly polymorphic, giving rise to the variance between individuals in the population. Id. Because of the key role of the antigen/MHC complex in the activation of T cells, inhibition of antigen binding to MHC molecules has been a goal of research in autoimmune diseases. Id.

In autoimmune diseases, inappropriate triggering of T cell responses by MHC molecule—"self antigen" complexes leads to destruction of normal tissues. Individuals inherit MHC genes of the HLA-DR, -DP, and -DQ haplotypes, and these have been linked to specific autoimmune diseases and autoantigens such as multiple sclerosis and rheumatoid arthritis. In each of these cases, patients diagnosed with the autoimmune disease carry an associated MHC gene. In rheumatoid arthritis, over 80% of patients have either HLA-DR1 or DR4 genes; in multiple sclerosis, ca. 70% have HLA-DR2.

Design of inhibitors of the cellular immune response has been a fundamental goal of research that aims to prevent T cell proliferation in autoimmune disease. Yusuf-Makagiansar et. al. (2002) *Med Res. Rev.* 22(2):146-167, Adorini, et al., (1988) *Nature,* 334, 623-625. For example, Astra-Zeneca has a partially stabilized, large peptide analog (ZD 2315) in phase II clinical trials that binds to DR1/4 based on these principles. The compound was shown to be active in vivo in mouse models. Cytel, Inc. developed a partially stabilized peptide (a(Cha)AAAKTAAAAa-NH$_2$) (SEQ ID NO.: 106) that binds DR molecules, but did not supress T cell proliferation in response to protein antigens, and also did not show activity in animal models of autoimmune disease (Lamont, et at. (1990), *J. Immnol.* 144, 2493-2498; Ishioka, et al., (1994) *J. Immunol.* 152, 4310-4319. The lack of cellular activity was thought to be inherent to peptides, because they are (a) susceptible to rapid exchange within the endosomal loading compartment in the presence of HLA-DM, and (b) are prone to cleavage by proteolyic enzymes of the cathepsin class that reside in the endosome to process protein antigens.

The interactions between peptides and MHC molecules have been defined in a series of high resolution crystal structures. Stem et al. (1994) *Nature* 368:215-221; Smith et al. (1998) *J. Exp. Med.* 188:1511-1520. The general observations include the extended, poly(proline) II helical conformation of the peptide backbone, the presence of pockets (that bind so-called anchor residues) along the chain, and networks of hydrogen bonds between the peptide backbone and side chains of the MHC molecules that line the binding site.

In other work, requirements for peptide binding have been assessed using structure-activity studies (Hammer, J. et al. (1993) *Cell* 74:197-203) with peptide phage display libraries.

2.2 Multiple Sclerosis

Multiple sclerosis is a chronic demyelinating autoimmune disease of the central nervous system that afflicts over 2 million patients worldwide, with approximately 350,000 patients in the U.S., with an average of 200 new patients diagnosed weekly. With the exception of trauma, multiple sclerosis is the leading cause of neurologic disability in early to middle adulthood. The disease is typically progressive, incapacitating, and affects multiple body systems. Accordingly, there remains a need for an effective treatment for multiple sclerosis in addition to other autoimmune diseases.

In multiple sclerosis, antigenic peptides derived from the myelin nerve sheath bind to the MHC class II molecule HLA-DR2. The specific allele, MHC class II HLA-DR2 (DRA*0101/DRB1*1501), has been closely associated with the multiple sclerosis. In people of northern European descent, approximately 70% of multiple sclerosis patients carry the HLA-DR2 gene. Giordano, M. et al. (2002) *Am. J. Pharmacogenomics* 2:37-58. Accordingly, compounds with the ability to inhibit antigen binding by the MHC class II HLA-DR2 are being sought as effective therapeutics for treating or preventing multiple sclerosis.

An additional study focused on the structural requirements for binding of a compound to DR2 molecules by probing peptides that comprise myelin basic protein ("MBP"). Wucherpfennig et al. (1994) *J. Exp. Med.* 179:279-290. The immunodominant MBP (84-102) peptide was found to bind with high affinity to DRB1*1501 and DRB5*0101 molecules of the disease-associated DR2 haplotype. Other peptide segments that overlapped with this peptide were also critical for binding to these molecules. It was demonstrated that hydrophobic residues (Val189 and Phe92) in the MBP (88-95) segment were critical for peptide binding to DRB1*1501 molecules and that hydrophobic and charged residues (Phe92, Lys93) in the MBP(89-101/102) sequence contributed to DRB5*0101 binding.

There remains a need for prophylactic or therapeutic drugs that can be used to treat or prevent autoimmune diseases, in particular multiple sclerosis. This invention addresses these and other needs in the pharmaceutical area.

3. SUMMARY OF THE INVENTION

In one embodiment, the invention relates to novel compounds that are useful as pharmaceuticals, particularly for the treatment or prevention of autoimmune diseases or disorders. In one embodiment, the compounds of the invention are useful for inhibiting antigen binding to MHC class II molecules both in vitro and in vivo, particularly MHC class II HLA-DR1, MHC class II HLA-DR2 or MHC class II HLA-DR4 molecules.

In another embodiment, the invention relates to compounds useful for inhibiting antigen presentation by MHC class II molecules, particularly a MHC class II HLA-DR1, MHC class II HLA-DR2 or MHC class II HLA-DR4 molecule.

In another embodiment, the invention relates to compounds useful for inhibiting T cell proliferation in animals, particularly mammals including humans.

In another embodiment, the invention relates to a method of treating or preventing a disease responsive to the inhibition of antigen binding to MHC class II molecules, particularly a MHC class II HLA-DR1, MHC class II HLA-DR2 or MHC class II HLA-DR4 molecule, comprising administering an effective amount of a compound of the invention to a patient in need thereof. In a preferred embodiment, the MHC class II HLA-DR molecule is a MHC class II HLA-DR2 molecule. The invention also relates to a method of inhibiting antigen binding to a MHC class II molecule comprising contacting a cell with an effective amount of a compound of the invention.

In another embodiment, the invention relates to a method of treating or preventing a disease responsive to the inhibition of antigen presentation by a MHC class II molecule, particularly a MHC class II HLA-DR1, MHC class II HLA-DR2 or MHC class II HLA-DR4 molecule, comprising administering an effective amount of a compound of the invention to a patient in need thereof. In a preferred embodiment, the MHC class II HLA-DR molecule is a MHC class II HLA-DR2 molecule. The invention also relates to a method of inhibiting antigen presentation by a MHC class II molecule comprising contacting a cell with an effective amount of a compound of the invention.

In another embodiment, the invention relates to a method of treating or preventing a disease responsive to the inhibition of T cell proliferation, comprising administering an effective amount of a compound of the invention to a patient in need thereof. The invention also relates to a method of inhibiting T cell proliferation comprising contacting a cell with an effective amount of a compound of the invention.

In another embodiment, the invention relates to a method of treating or preventing an autoimmune disease or disorder comprising administering an effective amount of a compound of the invention to a patient in need thereof.

4. DETAILED DESCRIPTION OF THE INVENTION

4.1 Definitions

As used herein, the term "patient" means an animal (e.g., cow, horse, sheep, pig, chicken, turkey, quail, cat, dog, mouse, rat, rabbit, guinea pig), preferably a mammal such as a non-primate and a primate (e.g., monkey and human), most preferably a human. In one embodiment, pre-screening is used to determine whether the patient possesses or is susceptible to having an immune, autoimmune or inflammatory disease or disorder by having a disease-associated MHC class II gene or genes.

As used herein, the term "substituted" means a group substituted by one to four or more substituents, such as, alkyl, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, alkylaminoalkyl, alkylamido, arylamino, aralkylamino, cycloalkylamino, heterocycloamino, mono and disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, hydroxy, hydroxyalkyl, alkoxyalkyl, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl.

As used herein, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. Unsaturated alkyl groups include alkenyl groups and alkynyl groups, which are discussed below.

As used herein, the term "alkenyl" means a straight chain or branched non-cyclic hydrocarbon having from 2 to 20 carbon atoms, more preferably 2-10 carbon atoms, most preferably 2-6 carbon atoms, and including at least one carbon-carbon double bond. Representative straight chain and branched ($C_2$-$C_{10}$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, the term "alkynyl" means a straight chain or branched non-cyclic hydrocarbon having from 2 to 20 carbon atoms, more preferably 2-10 carbon atoms, most preferably 2-6 carbon atoms, and including at lease one carbon-carbon triple bond. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, the term "acyl" means an alkanoyl or aroyl group, including acetyl, benzoyl, pivaloyl, cinnamoyl, and the like.

As used herein, the term "halogen" or "halo" means fluorine, chlorine, bromine, or iodine.

As used herein, the term "sulfonamido" means aryl-SONH— or alkyl-SONH, wherein aryl and alkyl are as defined above, including benzenesulfonamido, methanesulfonamido, and the like.

As used herein, the term "alkyl sulfonyl" means —$SO_2$-alkyl, wherein alkyl is defined as above, including —$SO_2$—$CH_3$, —$SO_2$—$CH_2CH_3$, —$SO_2$—$(CH_2)_2CH_3$, —$SO_2$—$(CH_2)_3CH_3$, —$SO_2$—$(CH_2)_4CH_3$, —$SO_2$—$(CH_2)_5CH_3$ and the like, and also includes alkyl sulfonic acid, including —$CH_2$—$SO_3H$, $(CH_2)_2$—$SO_3H$, and the like.

As used herein, the term "carboxyl" and "carboxy" mean —$COO^-$.

As used herein, the term "alkoxy" means —O-(alkyl), wherein alkyl is defined above, including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

As used herein, the term "alkoxycarbonyl" means —C(=O)O-(alkyl), wherein alkyl is defined above, including —C(=O)O—$CH_3$, —C(=O)O—$CH_2CH_3$, —C(=O)O—$(CH_2)_2CH_3$, —C(=O)O—$(CH_2)_3CH_3$, —C(=O)O—$(CH_2)_4CH_3$, —C(=O)O—$(CH_2)_5CH_3$, and the like. In a preferred embodiment, the esters are biohydrolyzable (i.e., the ester is hydrolyzed to a carboxylic acid in vitro or in vivo).

As used herein, the term "alkoxyalkyl" means -(alkyl)-O-(alkyl), wherein each "alkyl" is independently an alkyl group as defined above, including —$CH_2OCH_3$, —$CH_2OCH_2CH_3$, —$(CH_2)_2OCH_2CH_3$, —$(CH_2)_2O(CH_2)_2CH_3$, and the like.

As used herein, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricylic compounds as well as benzo-fused carbocyclic moieties such as 5,6,7,8-tetrahydronaphthyl and the like. Preferably, the aryl group is a monocyclic ring, bicyclic ring or tricyclic ring. Representative aryl groups include, but are not limited to, phenyl, tolyl, anthracenyl, fluorenyl, indenyl, azulenyl, phenanthrenyl and naphthyl. A carbocyclic aryl group can be unsubstituted or substituted.

As used herein, the term "heteroatom" means an atom other than carbon, and in a specific embodiment N, O or S.

As used herein, the term "heteroatom group" means a group containing one or more heteroatoms, C and H, including carboxamido, amindino, imino, guanidino, ureido, carbamoyl, and the like.

As used herein, the term "heteroaryl" means an aromatic ring containing from 5 to 14 ring atoms and the ring atoms contain at least one heteroatom, preferably 1 to 3 heteroatoms, independently selected from nitrogen, oxygen, or sulfur. Heteroaryl ring structures include compounds having one or more ring structures such as mono-, bi-, or tricyclic compounds as well as fused heterocyclic moieties. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl, oxetanyl, azepinyl, piperazinyl, morpholinyl, dioxanyl, thietanyl and oxazolyl. A heteroaryl group can be unsubstituted or substituted.

As used herein, the term "carbocyclic" means a carbocyclic ring containing from 5 to 14 ring atoms. The ring atoms of a carbocyclic group are all carbon atoms. Carbocyclic ring structures include compounds having one or more ring structures such as mono-, bi-, or tricylic compounds as well as fused carbocyclic and aryl moieties such a naphthalene, anthracene, indane, indene, phenalene, phenanthrene, benzocyclobutane, benzocycloheptane, tetrahydronaphthalene, and the like. Preferably, the carbocyclic group is a monocyclic ring, bicyclic ring or tricyclic ring. Representative carbocyclic groups include, but are not limited to, cyclopropyl, cyclobutyl, cyclopentyl, cyclohexyl, cycloheptyl, cyclooctyl and the like. A carbocyclic aryl group can be unsubstituted or substituted.

As used herein, the term "heterocyclic" means an ring containing from 5 to 14 ring atoms and the ring atoms contain at least one heteroatom, preferably 1 to 3 heteroatoms per ring, independently selected from nitrogen, oxygen, or sulfur. Heterocyclic ring structures include compounds having one or more ring structures such as mono-, bi-, or trycylic compounds as well as fused heterocyclic moieties. Representative heterocyclics include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, imidazolidinyl, isoxazolidinyl, isothiazolidinyl, oxazinanyl, piperazinyl, thiazinanyl, quinolinyl, chromenyl, oxathiolanyl and the like. A heterocyclic group can be unsubstituted or substituted.

As used herein, the term "bicyclic" means a two-ringed system containing from 9-14 carbon atoms wherein one or more, preferably 1-4 or 1-2, of the carbon atoms may be replaced with a heteroatom such as O, N or S. The bicyclic ring system may be saturated, unsaturated, aromatic or non-aromatic. Representative bicyclic rings include, but are not limited to, indole, isoquinoline, quinoline, tetrahydroisoquinoline, and benzofuran.

As used herein, the term "tricyclic" means a three-ringed system containing from 13-17 carbon atoms wherein one or more, preferably 1-6 or 1-3, of the carbon atoms may be replaced with a heteroatom such as O, N or S. The tricyclic ring system may be saturated, unsaturated, aromatic or non-aromatic. Representative tricyclic rings include, but are not limited to, carbazole, phenothiazine, dibenzofuran and fluorene.

As used herein, the term "aryloxy" means —O-aryl group, wherein aryl is as defined above. An aryloxy group can be unsubstituted or substituted.

As used herein, the term "arylalkyl" means -(alkyl)-(aryl), wherein alkyl and aryl are defined above, including —(CH$_2$)phenyl, —(CH$_2$)$_2$phenyl, —(CH$_2$)$_3$phenyl, —CH(phenyl)$_2$, —CH(phenyl)$_3$, —(CH$_2$)tolyl, —(CH$_2$)anthracenyl, —(CH$_2$)fluorenyl, —(CH$_2$)indenyl, —(CH$_2$)azulenyl, —(CH$_2$)pyridinyl, —(CH$_2$)naphthyl, and the like.

As used herein, the term "heteroarylalkyl" means -(alkyl)-(heteroaryl), wherein alkyl and heteroaryl are defined above, including —CH$_2$-triazolyl, —CH$_2$-tetrazolyl, —CH$_2$-oxadiazolyl, —CH$_2$-pyridyl, —CH$_2$-furyl, —(CH$_2$)$_2$-furyl, —CH$_2$-benzofuranyl, —CH$_2$-thiophenyl, —CH$_2$-benzothiophenyl, —CH$_2$-quinolinyl, —CH$_2$-pyrrolyl, —CH$_2$-indolyl, —CH$_2$-oxazolyl, —CH$_2$-benzoxazolyl, —CH$_2$-imidazolyl, —(CH$_2$)$_2$-imidazolyl, —CH$_2$-benzimidazolyl, —CH$_2$-thiazolyl, —CH$_2$-benzothiazolyl, —CH$_2$-isoxazolyl, —CH$_2$-pyrazolyl, —CH$_2$-isothiazolyl, —CH$_2$-pyridazinyl, —CH$_2$-pyrimidinyl, —CH$_2$-pyrazinyl, —CH$_2$-triazinyl, —CH$_2$-cinnolinyl, —CH$_2$-phthalazinyl, —CH$_2$-quinazolinyl, —CH$_2$-pyrimidyl, —CH$_2$-oxetanyl, —CH$_2$-azepinyl, —CH$_2$-piperazinyl, —CH$_2$-morpholinyl, —CH$_2$-dioxanyl, —CH$_2$-thietanyl, —CH$_2$-oxazolyl, —(CH$_2$)$_2$-triazolyl, and the like.

As used herein, the term "heteroalkyl" means an alkyl group, as defined above, wherein one or more of the —CH$_2$— groups is replaced with a heteroatom independently selected from nitrogen, oxygen, or sulfur, including ether, thioether and alkylamino groups such as —CH$_2$—O—CH$_3$, —CH$_2$—S—CH$_3$, —CH$_2$—NH—CH$_3$, —CH$_2$—O—CH$_2$—CH$_3$, —CH$_2$—S—CH$_2$—CH$_3$, —CH$_2$—NH—CH$_2$—CH$_3$, —CH$_2$—O—(CH$_2$)$_2$—CH$_3$, —CH$_2$—S—(CH$_2$)$_2$—CH$_3$, —CH$_2$NH—(CH$_2$)$_2$—CH$_3$, —CH$_2$—O—(CH$_2$)$_3$—CH$_3$, —CH$_2$—S—(CH$_2$)$_3$—CH$_3$, —CH$_2$—NH—(CH$_2$)$_3$—CH$_3$ including guanidino, amidino and the like.

As used herein, the term "hydroxyalkyl" means alkyl, wherein alkyl is as defined above, having one or more hydrogen atoms replaced with hydroxy, including —CH$_2$OH, —CH$_2$CH$_2$OH, —(CH$_2$)$_2$CH$_2$OH, —(CH$_2$)$_3$CH$_2$OH, —(CH$_2$)$_4$CH$_2$OH, —(CH$_2$)$_5$CH$_2$OH, —CH(OH)—CH$_3$, —CH$_2$CH(OH)CH$_3$, and the like.

As used herein, the term "hydroxy" means —OH.

As used herein, the term "oxoarylalkyl" means —O-(alkyl)-(aryl), wherein alkyl and aryl are defined above, including —O—(CH$_2$)$_2$phenyl, —O—(CH$_2$)$_3$phenyl, —O—CH(phenyl)$_2$, —O—CH(phenyl)$_3$, —O—(CH$_2$)tolyl, —O—(CH$_2$)anthracenyl, —O—(CH$_2$)fluorenyl, —O—(CH$_2$)indenyl, —O—(CH$_2$)azulenyl, —O—(CH$_2$)pyridinyl, —O—(CH$_2$)naphthyl, and the like.

As used herein, the term "cycloalkyloxy" means —O-(cycloalkyl), wherein cycloalkyl is defined above.

As used herein, the term "cycloalkylalkyloxy" means —O-(alkyl)-(cycloalkyl), wherein cycloalkyl and alkyl are defined above, including —O-cyclopropyl, —O-cyclobutyl, —O-cyclopentyl, —O-cyclohexyl, —O-cycloheptyl and the like.

As used herein, the term "aminoalkoxy" means —O-(alkyl)-NH$_2$, wherein alkyl is defined above, including —O—CH$_2$—NH$_2$, —O—(CH$_2$)$_2$—NH$_2$, —O—(CH$_2$)$_3$—NH$_2$, —O—(CH$_2$)$_4$—NH$_2$, —O—(CH$_2$)$_5$—NH$_2$, and the like.

As used herein, the term "alkylamino" means —NH-(alkyl) or —N-(alkyl)(alkyl), wherein alkyl is defined above, including —NH—CH$_3$, —NH—CH$_2$CH$_3$, —NH—(CH$_2$)$_2$CH$_3$, —NH—(CH$_2$)$_3$CH$_3$, —NH—(CH$_2$)$_4$CH$_3$, —NH—(CH$_2$)$_5$CH$_3$, —N—(CH$_3$)$_2$, —N—(CH$_2$CH$_3$)$_2$, —N—((CH$_2$)$_2$CH$_3$)$_2$, —N—(CH$_3$)(CH$_2$CH$_3$), and the like.

As used herein, the term "alkylamido" means -(alkyl)-NH—C(O)(alkyl), wherein each "alkyl" is independently an alkyl group defined above including —CH$_2$—NH—C(O)CH$_3$, —CH$_2$—NH—C(O)CH$_2$CH$_3$, —CH$_2$—NH—C(O)(CH$_2$)$_2$CH$_3$, —CH$_2$—NH—C(O)(CH$_2$)$_3$CH$_3$, —CH$_2$—NH—C(O)(CH$_2$)$_4$CH$_3$, —CH$_2$—NH—C(O)(CH$_2$)$_5$CH$_3$, —(CH$_2$)$_2$—NH—C(O)CH$_3$, —(CH$_2$)$_2$—NH—C(O)CH$_2$CH$_3$, —(CH$_2$)$_2$—NH—C(O)(CH$_2$)$_2$CH$_3$, and the like or -(alkyl)-C(O)—NH-(alkyl), wherein each "alkyl" is independently an alkyl group defined above including —CH$_2$—C(O)—NH—CH$_3$, —CH$_2$—C(O)—NH—CH$_2$CH$_3$, —CH$_2$—C(O)—NH—(CH$_2$)$_2$CH$_3$, —CH$_2$—C(O)—NH—(CH$_2$)$_3$CH$_3$, —CH$_2$—C(O)—NH—(CH$_2$)$_4$CH$_3$, —CH$_2$—C(O)—NH—(CH$_2$)$_5$CH$_3$, —(CH$_2$)$_2$—C(O)—NH—CH$_3$, —(CH$_2$)$_2$—C(O)—NH—CH$_2$CH$_3$, —(CH$_2$)$_2$—C(O)—NH—(CH$_2$)$_2$CH$_3$, and the like.

As used herein, the term "dialkylaminoalkyl" means -(alkyl)-N(alkyl)(alkyl), wherein each "alkyl" is independently an alkyl group defined above, including —CH$_2$—N(CH$_3$)$_2$, —CH$_2$—N(CH$_2$CH$_3$)$_2$, —CH$_2$—N((CH$_2$)$_2$CH$_3$)$_2$, —CH$_2$—N(CH$_3$)(CH$_2$CH$_3$), —(CH$_2$)$_2$—N(CH$_3$)$_2$, and the like.

As used herein, the term "arylamino" means —NH(aryl), wherein aryl is defined above, including —NH(phenyl), —NH(tolyl), —NH(anthracenyl), —NH(fluorenyl), —NH(indenyl), —NH(azulenyl), —NH(pyridinyl), —NH(naphthyl), and the like.

As used herein, the term "arylalkylamino" means —NH-(alkyl)-(aryl), wherein alkyl and aryl are defined above, including —NH—CH2-(phenyl), —NH—CH$_2$-(tolyl), —NH—CH$_2$-(anthracenyl), —NH—CH$_2$-(fluorenyl), —NH—CH$_2$-(indenyl), —NH—CH$_2$-(azulenyl), —NH—CH$_2$-(pyridinyl), —NH—CH$_2$-(naphthyl), —NH—(CH$_2$)$_2$-(phenyl) and the like.

As used herein, the term "cycloalkylamino" means —NH-(cycloalkyl), wherein cycloalkyl is defined above, including —NH-cyclopropyl, —NH-cyclobutyl, —NH-cyclopentyl, —NH-cyclohexyl, —NH-cycloheptyl, and the like.

As used herein, the term "aminoalkyl" means -(alkyl)-NH$_2$, wherein each "alkyl" is independently an alkyl group defined above, including —CH$_2$—NH$_2$, —(CH$_2$)$_2$—NH$_2$, —(CH$_2$)$_3$—NH$_2$, —(CH$_2$)$_4$—NH$_2$, —(CH$_2$)$_5$—NH$_2$ and the like.

As used herein, the term "alkylaminoalkyl" means -(alkyl)-NH(alkyl) or -(alkyl)-N(alkyl)(alkyl), wherein each "alkyl" is independently an alkyl group defined above, including —CH$_2$—NH—CH$_3$, —CH$_2$—NHCH$_2$CH$_3$, —CH$_2$—NH(CH$_2$)$_2$CH$_3$, —CH$_2$—NH(CH$_2$)$_3$CH$_3$, —CH$_2$—NH(CH$_2$)$_4$CH$_3$, —CH$_2$—NH(CH$_2$)$_5$CH$_3$, —(CH$_2$)$_2$—NH—CH$_3$, —CH$_2$—N(CH$_3$)$_2$, —CH$_2$—N(CH$_2$CH$_3$)$_2$, —CH$_2$—N((CH$_2$)$_2$CH$_3$)$_2$, —CH$_2$—N(CH$_3$)(CH$_2$CH$_3$), —(CH$_2$)$_2$—N(CH$_3$)$_2$, and the like.

As used herein, the term "alkoxyaminoalkyl" means —O-alkyl-NH(alkyl) or —O-alkyl-N(alkyl)(alkyl), where alkyl and aminoalkyl are as defined above, including —OCH$_2$CH$_2$N(CH$_3$)$_2$, and the like.

As used herein, the term "sugar moiety" means monosaccharides (e.g., glucose, arabinose, fucose, galactose, mannose, xylose, fructose, lyxose, allose, arinose, ribose, talose, gulose, idose, altrose, sorbitol, mannitol or glucosamine), disaccharides and oligosaccharides (e.g., maltose, isomaltose, turanose, gentiobiose, melibiose, planteobiose, primerose, vicianose, nigerose, laminaribiose, rutinose, cellobiose, xylobiose, maltotriose, gentianose, melezitose, planteose, ketose, trehalose, sucrose, lactose, raffinose or xylotriose), polysaccharides (e.g., amylose, ficol, dextrin, starch, dextran, polydextrose, pullulan, cyclodextrin, glucomannoglycan, glucomannan, guar gum, gum arabic or glycosaminoglycan), complex carbohydrates (e.g., glycopeptide, glycoprotein, glycolipid or proteoglycan), and the like.

As used herein, the term "PEG" means a polyethylene glycol group such as $H(OCH_2CH_2)_nOH$, wherein n is 1-30, 1-25, 1-20, 1-15, 1-10, 1-5 or 1-2.

As used herein, a "therapeutically effective amount" refers to that amount of the compound of the invention or other active ingredient sufficient to provide a therapeutic benefit in the treatment or management of the disease (e.g., a genetic disease, a central nervous system ("CNS") disease, an inflammatory disease, a neurodegenerative disease or an autoimmune disease) or to delay or minimize symptoms associated with the disease. Further, a therapeutically effective amount with respect to a compound of the invention means that amount of therapeutic agent alone, or in combination with other therapies, that provides a therapeutic benefit in the treatment or management of the disease. Used in connection with an amount of a compound of the invention, the term can encompass an amount that improves overall therapy, reduces or avoids symptoms or causes of disease, or enhances the therapeutic efficacy of or synergies with another therapeutic agent.

As used herein, a "prophylactically effective amount" refers to that amount of a compound of the invention or other active ingredient sufficient to result in the prevention, recurrence or spread of the disease (e.g., a genetic disease, a CNS disease, an inflammatory disease, a neurodegenerative disease or an autoimmune disease). A prophylactically effective amount may refer to the amount sufficient to prevent initial disease or the recurrence or spread of the disease or the occurrence of the disease in a patient, including but not limited to those predisposed to the disease. A prophylactically effective amount may also refer to the amount that provides a prophylactic benefit in the prevention of the disease. Further, a prophylactically effective amount with respect to a compound of the invention means that amount alone, or in combination with other agents, that provides a prophylactic benefit in the prevention of the disease. Used in connection with an amount of a compound of the invention, the term can encompass an amount that improves overall prophylaxis or enhances the prophylactic efficacy of or synergies with another prophylactic agent.

As used herein, a "therapeutic protocol" refers to a regimen of timing and dosing of one or more therapeutic agents.

As used herein, a "prophylactic protocol" refers to a regimen of timing and dosing of one or more prophylactic agents.

A used herein, a "protocol" includes dosing schedules and dosing regimens.

As used herein, "in combination" refers to the use of more than one prophylactic and/or therapeutic agent on a patient in a manner such that the patient benefits from both drugs. The drugs may be administered simultaneously or sequentially. In one embodiment, the compound of the invention and the other prophylactic or therapeutic agent exert their biological effect on the patient during the same time period.

As used herein, the terms "prevent", "preventing" and "prevention" refer to the prevention of the onset, recurrence, or spread of the disease (e.g., a genetic disease, a CNS disease, an inflammatory disease, a neurodegenerative disease or an autoimmune disease) in a patient. In one embodiment, the patient shows signs of an autoimmune disease, particularly multiple sclerosis, or has a first lesion, and administration of a compound of the invention prevents worsening of the symptoms or the formation of additional lesions.

As used herein, the terms "treat", "treating" and "treatment" refer to the eradication or amelioration of the disease (e.g., a genetic disease, a CNS disease, an inflammatory disease, a neurodegenerative disease or an autoimmune disease) or symptoms associated with the disease or to the management of the disease which does not result in a cure of the disease or reduction of the disease but prevents its progression. In certain embodiments, such terms refer to minimizing the spread or worsening of the disease resulting from the administration of one or compounds of the invention to a patient with such a disease. In one embodiment, a patient is administered one or more compounds of the invention to manage a disease so as to prevent the progression or worsening of the disease.

As used herein, the term "pharmaceutically acceptable salts" refer to salts prepared from pharmaceutically acceptable non-toxic acids or bases including inorganic acids and bases and organic acids and bases. Suitable pharmaceutically acceptable base addition salts for the compound of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein, the term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, biohydrolyzable lipids and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "optically pure" or "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, the term "enantiomerically pure" means a stereomerically pure composition of a compound having one or more chiral centers.

As used herein, the term "compound of the invention" means a compound described herein which is capable of inhibiting antigen binding to an MHC class II HLA-DR 1, 2 or 4 molecule or inhibiting T cell proliferation in vitro or in vivo. Such inhibitory activity can be determined by an assay or animal model well-known in the art including those set forth in Section 5. The compound of the invention can be in the form of a pharmaceutically acceptable prodrug, salt, solvate or hydrate thereof. The compounds of the invention may also be "capped" wherein the cap is a group such as an acyl group, sulfonyl group, group containing a PEG group, a sugar moiety, or an alkyl group substituted with one or more hydroxy groups. Examples of capping groups include, but are not limited to, —NHCH$_3$, —NHAc, —CO$_2$R, —CO$_2$Ac and —CO$_2$NR$_2$ (wherein each occurrence of R is independently H or alkyl). Further examples of capping groups include those disclosed in U.S. Pat. No. 6,020,315, issued Feb. 1, 2000, incorporated by reference herein in its entirety. In a preferred embodiment, the compound of the invention is a compound of structure I-IV.

As used herein, the terms "naturally occurring amino acid" or "natural amino acid" refer to any of the 20 naturally occurring L-amino acids as set forth in Table 1, below, and also include mixtures which contain about 0.1%, about 0.5%, about 1%, about 5%, about 10%, about 25%, about 50%, about 75%, about 90%, about 95%, about 99%, about 99.5% or about 99.9% by weight of the corresponding D-amino acid. The amino acids can be used to prepare or are a part of the compounds of the invention. The linkage between each amino acid of the compounds of the invention may be an amide, a substituted amide or an isostere of amide.

TABLE 1

Abbreviations for natural L-amino acids

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the terms "non-naturally occurring amino acid" or "non-natural amino acid" refers to any natural amino acid that has been modified or any structure having amino and carboxyl groups (e.g., ornithine), including peptide mimetics encompassing more than one amino acid in length, or non-peptide peptide mimetics having backbone replacements for the peptide backbone, represented by $P_1, P_2, P_3, P_4, P_5, P_6, P_7, P_8, P_9, P_{10}$, below. Addition mimetic groups which can be incorporated into the compounds of the invention include those disclosed in Gillespie et al. (1997) *Biopolym. Pep. Science* 43:191. Non-natural amino acids also include D-isomers of the amino acids set forth in Table 1. The present invention further encompasses compounds which can be comprised of both D and L isomers of non-natural amino acids as well as other isomeric forms of the non-natural amino acids (e.g., geometric isomers, positional isomers and stereoisomers).

Non-classical amino acids or chemical amino acid analogues are also used to prepare or are a part of the compounds of the invention. Non-classical amino acids include, but are not limited to, the D-isomers (R-configuration) of the common amino acids, α-O-amino isobutyric acid, 4-aminobutyric acid, Abu, 2-amino butyric acid, (-Abu, -Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-O-alanine, fluoro-amino acids, designer amino acids such as β-O-methyl amino acids, Cα-O-methyl amino acids, Nα-O-methyl amino acids, and amino acid analogues in general. Furthermore, the amino acid or non-classical amino acids or analogues can have R- or S-configurations. More specifically, the invention includes compounds comprised of either enantionmer of an amino acid, non-natural amino acid, non-classical amino acid or chemical amino acid analogue. With respect to the use of non-natural amino acids, non-classical amino acids and chemical amino acid analogues, the stereochemical variation is robust and the invention encompasses compounds comprising one or more enantiomers or epimers at one or more of the $K_1, K_2$ or $P_1$-$P_{10}$ positions.

4.2 Compounds of the Invention

The present invention provides compounds of formulas I-IV ("compound(s) of the invention"), pharmaceutical compositions comprising the compounds of the invention and methods of their use. Without being limited by theory, the compounds of the invention are thought to be modulators of antigen presentation by HLA-DR class II MHC molecules.

In one embodiment, the compounds of the invention are those of formula I:

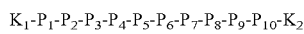

or a pharmaceutically acceptable salt thereof, wherein:

$K_1$ is an optional substituent that, when present, is alkyl-C(O)—, hydroxyalkyl-C(O)—, aralkyl-C(O)—, heteroarylalkyl-C(O), alkoxy-C(O)—, alkoxycarbonylalkyl-C(O)—, amino-C(O)—, monoalkylamino-C(O)—, dialkylamino-C(O)—, aminoalkyl-C(O)—, monoalkylaminoalkyl-C(O)—, dialkylaminoalkyl-C(O)—, $NH_2(CH_2)_4C(O)$—, $NH_2(CH_2)_3C(O)$—, hydroxyalkyl, sulfonyl, aminosulfonyl, alkylaminosulfonyl, dialkylaminosulfonyl, arylsulfonyl, or a sugar moiety;

$P_1$-$P_{10}$ are optional substituents that, when present, are each independently amino acyl groups of a natural amino acid or a non-natural amino acid including those set forth in Table 2 (wherein n is an integer ranging from 1 to 4), below, wherein at least three of $P_1$-$P_{10}$ are present and at least one of $P_1$-$P_{10}$, or at least two of $P_1$-$P_{10}$, or at least three of $P_1$-$P_{10}$, or at least four of $P_1$-$P_{10}$, or at least five of $P_1$-$P_{10}$, or at least six of $P_1$-$P_{10}$, or at least seven of $P_1$-$P_{10}$, or at least eight of $P_1$-$P_{10}$, or at least nine of $P_1$-$P_{10}$ or all of $P_1$-$P_{10}$ is a non-natural amino acid or peptide mimetic;

$K_2$ is an optional substituent, that, when present, is —OH (forming an amino acid group with $P_{10}$), amino (forming an amino acid amide with $P_{10}$), or amino group substituted with linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, and the like.

In one embodiment, the compounds of formula I have 2-10 or 3-10 P groups. In another embodiment, the compounds of formula I have 2-8 or 3-8 P groups. In another embodiment, the compounds of formula I have 2-6 or 3-6 P groups. In another embodiment, the compounds of formula I have 2-4 or 3-4 P groups. In another embodiment, the compounds of formula I have 4-8 P groups. In another embodiment, the compounds of formula I have 4-6 P groups.

In one embodiment, the compounds of formula I contain all L residues.

In one embodiment, the compounds of formula I contain one or more, two or more, three or more, four or more, five or more, six or more, seven or more eight or more, or nine or more residues in the D configuration. In another embodiment, the compounds of formula I contain all D residues.

In one embodiment, $P_8$-$P_{10}$ include any of the groups set forth in Table 2, below.

Illustrative non-limiting examples of $P_1$-$P_{10}$ include a contiguous sequence of residues selected from those described in Table 2 (wherein n is an integer ranging from 1 to 4), below.

TABLE 2

TABLE 2-continued
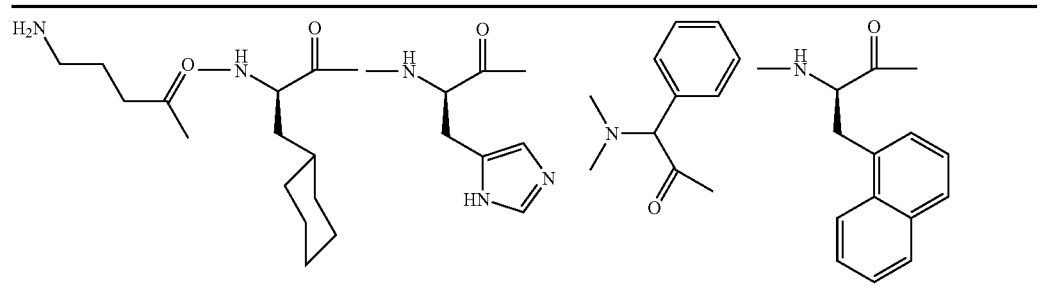
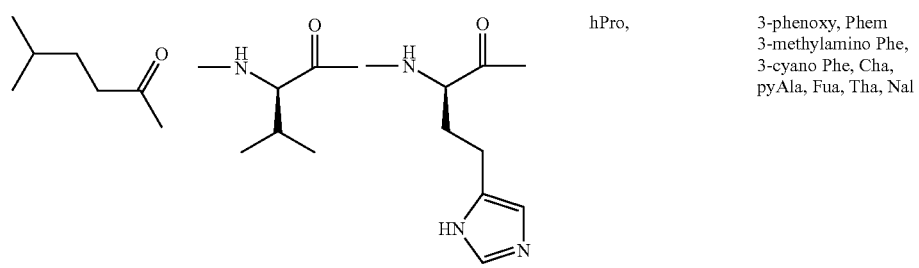
| | | | | 3-phenoxy, Phem 3-methylamino Phe, 3-cyano Phe, Cha, pyAla, Fua, Tha, Nal |
|---|---|---|---|---|
| K₁-{aa}- Where aa is any natural or unnatural amino acid | Ileu, Leu, Phe, Chg, Fua, Tha | Dab, pyAla | hPro, | |
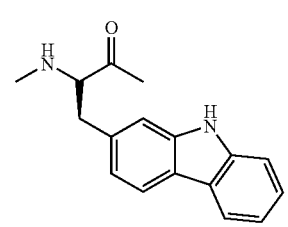
| K₁ | P(n+4) | P(n+5) | P(n+6) | K₂ |
|---|---|---|---|---|
| | | | | H, NH₂, NHCH₃, N(CH₃)₂, |

TABLE 2-continued
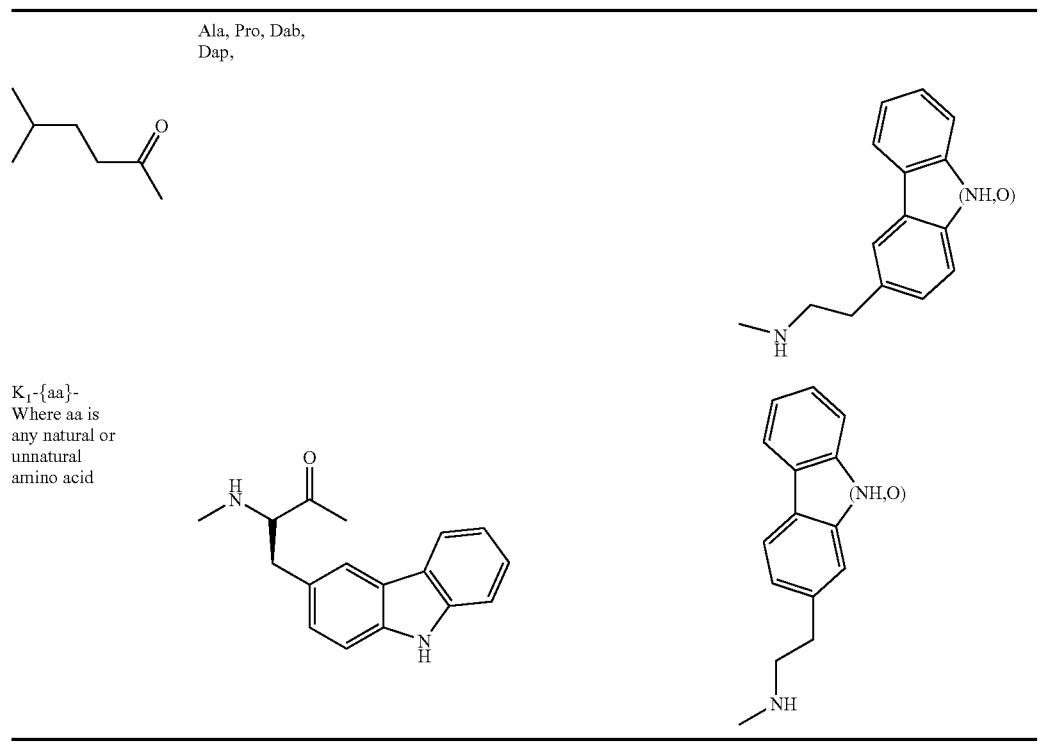
K₁-{aa}-
Where aa is
any natural or
unnatural
amino acid
Wherein the above abbreviations represent the following structures:
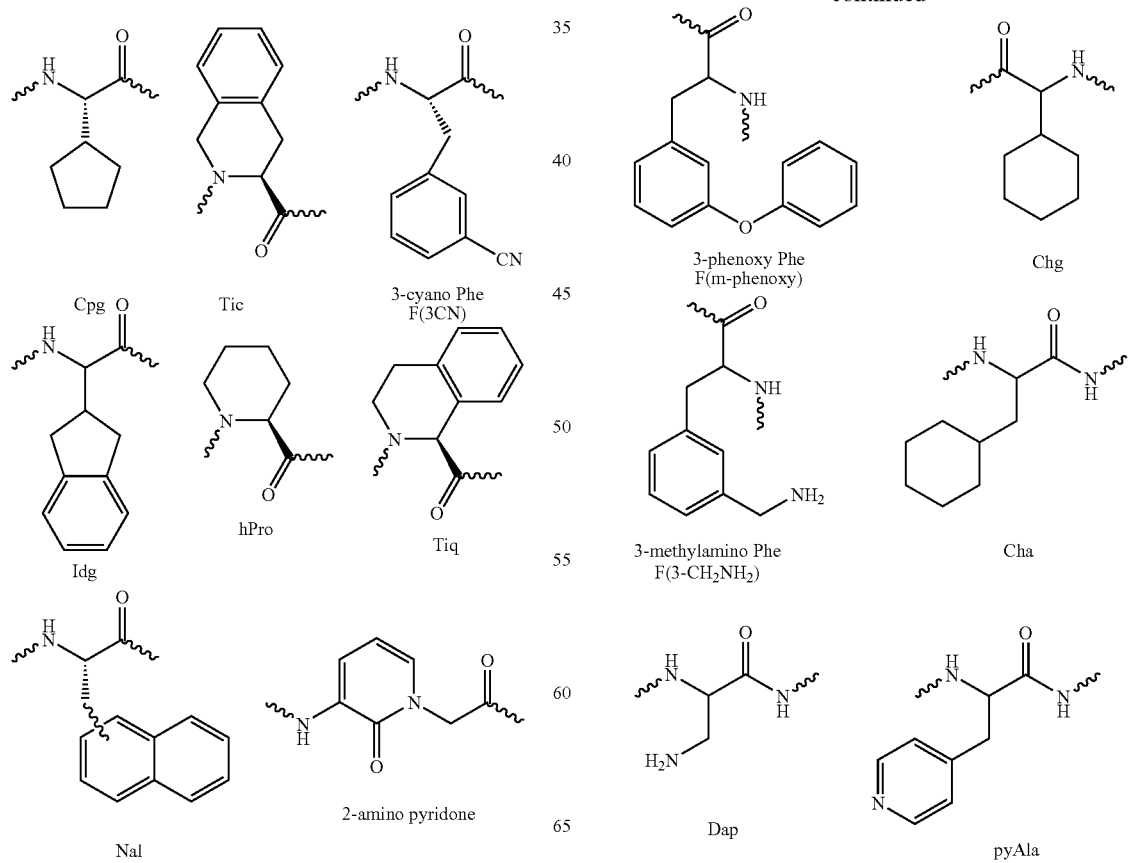

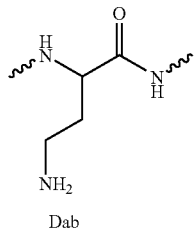

Dab

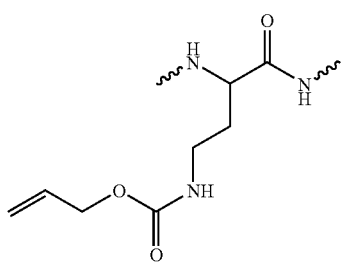

Dab (Alloc)

-continued

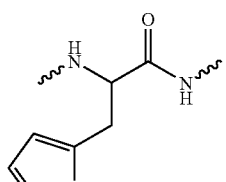

Fua

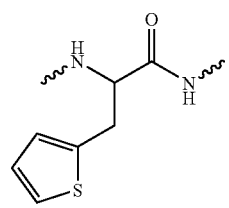

Tha

In addition, each of the following formulas are included as illustrative examples of compounds of the invention:

$K_1$-$P_1$-$P_2$-$P_3$-$P_4$-$P_5$-$P_6$-$P_7$-$P_8$-$P_9$-$K_2$;
$K_1$-$P_1$-$P_2$-$P_3$-$P_4$-$P_5$-$P_6$-$P_7$-$P_8$-$K_2$;
$K_1$-$P_1$-$P_2$-$P_3$-$P_4$-$P_5$-$P_6$-$P_7$-$K_2$;
$K_1$-$P_1$-$P_2$-$P_3$-$P_4$-$P_5$-$P_6$-$K_2$;
$K_1$-$P_1$-$P_2$-$P_3$-$P_4$-$P_5$-$K_2$;
$K_1$-$P_1$-$P_2$-$P_3$-$P_4$-$K_2$;
$K_1$-$P_1$-$P_2$-$P_3$-$K_2$;
$K_1$-$P_2$-$P_3$-$P_4$-$P_5$-$P_6$-$P_7$-$P_8$-$P_9$-$P_{10}$-$K_2$;
$K_1$-$P_3$-$P_4$-$P_5$-$P_6$-$P_7$-$P_8$-$P_9$-$P_{10}$-$K_2$;
$K_1$-$P_4$-$P_5$-$P_6$-$P_7$-$P_8$-$P_9$-$P_{10}$-$K_2$;
$K_1$-$P_5$-$P_6$-$P_7$-$P_8$-$P_9$-$P_{10}$-$K_2$;
$K_1$-$P_6$-$P_7$-$P_8$-$P_9$-$P_{10}$-$K_2$;
$K_1$-$P_7$-$P_8$-$P_9$-$P_{10}$-$K_2$; and
$K_1$-$P_8$-$P_9$-$P_{10}$-$K_2$.

Without being limited by theory, in one embodiment, the minimum active formula comprises $K_1$, $K_2$ and three P groups (e.g., $K_1$-$P_{(1-10)}$-$P_{(1-10)}$-$P_{(1-10)}$-$K_2$). In another embodiment, $K_1$, and $K_2$ are optional in the minimum active formula.

In another embodiment, the compounds of the invention are those of formula II:

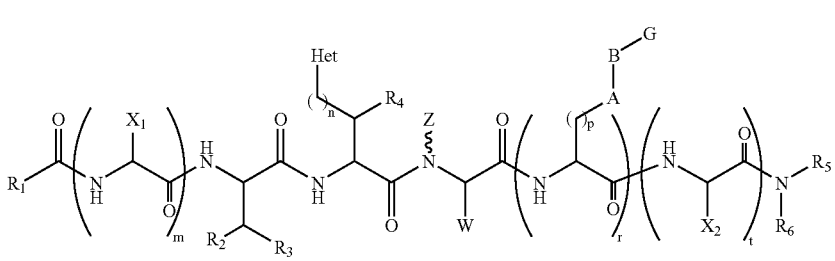

II or a pharmaceutically acceptable salt thereof, wherein:

$R_1$ is linear or branched alkyl, PEG, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino, guanidino, hydroxyalkyl or a sugar moiety;

$X_1$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidino;

$X_2$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidino;

$R_2$ and $R_3$ are independently hydrogen, linear or branched alkyl, alkoxy, alkoxyalkyl; or $R_2$ and $R_3$ taken together form a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring; or $R_2$ and $R_3$ taken together form a substituted or unsubstituted bicyclic ring;

$R_4$ is hydrogen, linear or branched alkyl, alkoxy, alkoxycarbonyl, hydroxyalkyl or hydroxy;

Het is a heteroatom containing group, such as —NH, —SH, —OH, heteroalkyl, alkylamino, aminoalkyl, alkylaminoalkyl, alkylamido, dialkylaminoalkyl, aminoalkoxy or a substituted or unsubstituted heterocyclic ring;

$R_5$ and $R_6$ are independently hydrogen, linear or branched alkyl, PEG, hydroxyalkyl, heteroalkyl, $CH_3C(O)$—, $NH_2(CH_2)_4C(O)$—, $NH_2(CH_2)_3C(O)$—, or a sugar moiety; or $R_5$ and $R_6$ taken together form a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring; or when r is 0 and t is 0, $R_6$ can be $(CH_2)_p$-A-B-G;

Z is hydrogen, linear or branched alkyl, heteroalkyl; or Z taken together with W can form a substituted or unsubstituted 5-7 membered carbocyclic ring, a substituted or unsubstituted 5-7 membered heterocyclic ring, a substituted or unsubstituted 5-7 membered heterocyclic aromatic ring, a substituted or unsubstituted 5-7 membered aromatic ring; or Z taken together with W can form a substituted or unsubstituted bicyclic ring;

W is linear or branched alkyl, substituted or unsubstituted aryl or substituted or unsubstituted arylalkyl;

A is a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring, a substituted or unsubstituted 9-14 membered bicyclic ring; or a substituted or unsubstituted 13-17 membered tricyclic ring;

B is an optional substituent that, when present, is —CHY—, —YCH—, —Y(CH)$_q$—, —(CH)$_q$Y—, YG- or GY—;

G is an optional substituent that, when present, is linear or branched alkyl, substituted or unsubstituted heteroalkyl, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring;

Y is O, S or $NR_2R_3$;

m is an integer between 0-3;

n is an integer between 0-4, such that —$CH_2$— is absent, present or in a chain of up four methyl groups;

r is an integer between 0-3;

t is an integer between 0-3;

p is an integer between 0-4, such that —$CH_2$— is absent, present or in a chain of up four methyl groups; and q is an integer between 1-3, wherein the compounds of formula II do not include an all natural L-amino acid peptide.

In one embodiment, the compounds of formula II contain all L residues.

In one embodiment, the compounds of formula II contain one or more, two or more, three or more, four or more, five or more, six or more, seven or more eight or more, or nine or more residues in the D configuration. In another embodiment, the compounds of formula II contain all D residues.

In a preferred embodiment, the compounds of the present invention are those of formula III:

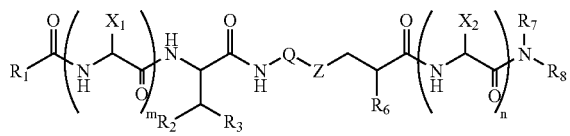

or a pharmaceutically acceptable salt thereof, wherein:

$R_1$ is linear or branched alkyl, PEG, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino, guanidino, hydroxyalkyl or a sugar moiety;

$X_1$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidino;

$X_2$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidine; or $(CH_2)_p$-A-B-G, as hereinbefore defined in formula II;

$R_2$ and $R_3$ are independently hydrogen, linear or branched alkyl, alkoxy, alkoxyalkyl; or $R_2$ and $R_3$ taken together form a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring; or $R_2$ and $R_3$ taken together form a substituted or unsubstituted 9-14 membered bicyclic ring;

Q is —$CH_2$, —$CHR_4$, —NH or —$NR_4$;

$R_4$ is hydrogen, linear or branched alkyl, alkoxy, hydroxyalkyl or hydroxy;

Z is —$CH_2$, —$C(O)$ or —CHOH when Q is —$CH_2$ or —$CHR_4$ and Z is —$CH_2$ or —$C(O)$ when Q is —NH or —$NR_4$;

$R_6$ is linear or branched alkyl, arylalkyl, heteroarylalkyl, alkoxy, alkoxyalkyl, oxoarylalkyl, aminoalkyl, alkylaminoalkyl, dialkylaminoalkyl, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring;

$R_7$ is hydrogen, linear or branched alkyl, PEG, hydroxyalkyl, heteroalkyl, $CH_3C(O)$—, $NH_2(CH_2)_4C(O)$—, $NH_2(CH_2)_3C(O)$—, a sugar moiety, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring;

$R_8$ is hydrogen, linear or branched alkyl, PEG, hydroxyalkyl, heteroalkyl, $CH_3C(O)$—, $NH_2(CH_2)_4C(O)$—, $NH_2(CH_2)_3C(O)$—, a sugar moiety, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring, or when n is 0, $R_8$ can be $(CH_2)_p$-A-B-G;

A is a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring, a substituted or unsubstituted 9-14 membered bicyclic ring; or a substituted or unsubstituted 13-17 membered tricyclic ring;

B is an optional substituent that, when present, is —CHY—, —YCH—, —Y(CH)$_q$—, —(CH)$_q$Y—, YG- or GY—;

G is an optional substituent that, when present, is linear or branched alkyl, substituted or unsubstituted heteroalkyl, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring;

Y is O, S or NR$_2$R$_3$;

m is an integer from 0-3;

n is an integer from 0-3;

p is an integer between 0-4; and q is an integer between 1-3, wherein the compounds of formula III do not include an all natural L-amino acid peptide.

In one embodiment, the compounds of formula IIII contain all L residues.

In one embodiment, the compounds of formula III contain one or more, two or more, three or more, four or more, five or more, six or more, seven or more eight or more, or nine or more residues in the D configuration. In another embodiment, the compounds of formula III contain all D residues.

In another preferred embodiment, the compounds of the present invention are those of formula IV:

R$_4$ is hydrogen, linear or branched alkyl, alkoxy, hydroxyalkyl or hydroxy;

Z is —CH$_2$, —C(O) or —CHOH when Q is —CH$_2$ or —CHR$_4$ and Z is -CH$_2$ or —C(O) when Q is —NH or —NR$_4$;

R$_6$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidino R$_7$ is linear or branched alkyl, arylalkyl, heteroarylalkyl, alkoxy, alkoxyalkyl, oxoarylalkyl, aminoalkyl, alkylaminoalkyl, dialkylaminoalkyl, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring, or (CH$_2$)$_p$-A-B-G, as hereinbefore defined in formula II;

R$_8$ is hydrogen, linear or branched alkyl, PEG, hydroxyalkyl, heteroalkyl, CH$_3$C(O)—, NH$_2$(CH$_2$)$_4$C(O)—, NH$_2$(CH$_2$)$_3$C(O)—, a sugar moiety, a substituted or unsubstituted 5-7 membered carbocyclic ring, a substituted or unsubstituted 5-7 membered heterocyclic ring, a substituted or unsubstituted 5-7 membered heteroaryl ring, a substituted or unsubstituted 5-7 membered aryl ring;

m is an integer between 0-3;

n is an integer between 0-3;

t is an interger between 1-4; and p is an integer between 0-4.

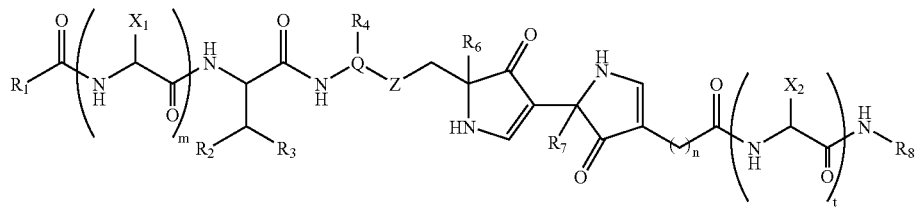

IV or a pharmaceutically acceptable salt thereof, wherein:

R$_1$ is linear or branched alkyl, PEG, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino, guanidino, hydroxyalkyl or a sugar moiety;

X$_1$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidino;

X$_2$ is linear or branched alkyl, hydroxyalkyl, heteroalkyl, arylalkyl, heteroarylalkyl, alkoxy, alkoxycarbonyl, alkoxyalkyl, oxoarylalkyl, aminoalkyl, alkylaminoalkyl, dialkylaminoalkyl, amidino or guanidino;

R$_2$ and R$_3$ are independently hydrogen, linear or branched alkyl, alkoxy, alkoxyalkyl; or R$_2$ and R$_3$ taken together form a substituted or unsubstituted 5-7 membered carbocyclic ring, a substituted or unsubstituted 5-7 membered heterocyclic ring, a substituted or unsubstituted 5-7 membered heteroaromatic ring, a substituted or unsubstituted 5-7 membered aryl ring; or R$_2$ and R$_3$ taken together form a substituted or unsubstituted 9-14 membered bicyclic ring;

Q is —CH$_2$, —CHR$_4$, —NH or —NR$_4$;

In one embodiment, the compounds of formula IV contain all L residues.

In one embodiment, the compounds of formula IV contain one or more, two or more, three or more, four or more, five or more, six or more, seven or more eight or more, or nine or more residues in the D configuration. In another embodiment, the compounds of formula IV contain all D residues.

In one embodiment, the compounds of formula I are those set forth in Table 3, below, or a pharmaceutically acceptable salt thereof, which are provided herein by way of illustration and not limitation.

TABLE 3

| Entry | Compound | SEQ ID NO |
|---|---|---|
| 1 | ENPVVHFFKNI | 1 |
| 2 | AcVHFFKNI | 2 |
| 3 | AcIHFFKNI | 3 |
| 4 | AcVRFFKNI | 4 |
| 5 | AcVHPFKNI | 5 |
| 6 | AcVHFFPNI | 6 |
| 7 | AcVHFFKTI | 7 |
| 8 | AcVRFANI | 8 |
| 9 | AcVRPFS | 9 |
| 10 | AcVRLFANI | 10 |

TABLE 3-continued

| Entry | Compound | SEQ ID NO |
|---|---|---|
| 11 | AcVVHFFKNI | 11 |
| 12 | AcVTFFKNI | 12 |
| 13 | AcVH(N—Me Ala)FKNI | 13 |
| 14 | AcVHA(N—Me Ala)-F-(N—Me Ala)N | 14 |
| 15 | AcVHFVKNI | 15 |
| 16 | AcVRF(2-Nal)KNI | 16 |
| 17 | AcVRF(1-Nal)KNI | 17 |
| 18 | AcVHFFA(N—Me Ala)NI | 18 |
| 19 | AcVRLFKN | 19 |
| 20 | AcVRF(4'-Pyridyl Ala)KNI | 20 |
| 21 | AcVRAFAN | 21 |
| 22 | AcVRA(O-Benzyl Ser)KNI | 22 |
| 23 | Ac(Tic)FKNI | 23 |
| 24 | AcVR(Tic)FKNI | 24 |
| 25 | Ac(Cpg)RFFKNI | 25 |
| 26 | AcVHSFSN | 26 |
| 27 | AcVRF(3' Cyano Phe)KNI | 27 |
| 28 | AcVR(Tiq)FKNI | 28 |
| 29 | Ac(Tiq)FKNI | 29 |
| 30 | AcVVRFFK | 30 |
| 31 | AcVRFF(homo Pro)NI | 31 |
| 32 | Ac(Tic)FKNI | 32 |
| 33 | Ac(Cpg)R(Tic)FKNI | 33 |
| 34 | AcVR(homo Pro)FKNI | 34 |
| 35 | AcVRFFK | 35 |
| 36 | AcVKFFKNI | 36 |
| 37 | AcV(Orn)FFKNI | 37 |
| 38 | AcV(N' Alloc Dab)FFKNI | 38 |
| 39 | Ac(Cha)RFFKNI | 39 |
| 40 | Ac(2' Furanyl Ala)RFFKNI | 40 |
| 41 | Ac(2' Thienyl Ala)RFFKNI | 41 |
| 42 | AcVR(2' Furanyl Ala)FKNI | 42 |
| 43 | AcVR(2' Thienyl Ala)FKNI | 43 |
| 44 | AcVRAFKNI | 44 |
| 45 | Benzoyl-VRFFK | 45 |
| 46 | Isobutanoyl-VRFFK | 46 |
| 47 | Butanoyl-VRFFK | 47 |
| 48 | IsoValeroyl-VRFFK | 48 |
| 49 | Ac(Cpg)R(Tic)F(homo Pro) | 49 |
| 50 | AcVVRFF | 50 |
| 51 | 3-(Imadazoyl-4-yl)propionyl-VRFFK | 51 |
| 52 | Ac(Chg)RFFKNI | 52 |
| 53 | AcVRFF(Dap)NI | 53 |
| 54 | AcV(Dab)FFKNI | 54 |
| 55 | AcVVAGFKNI | 55 |
| 56 | AcVAGFKNI | 56 |
| 57 | AcV(Dap)FFKNI | 57 |
| 58 | AcVRFF | 58 |
| 59 | AcVRF(3' phenoxy Phe)KNI | 59 |
| 60 | AcVVKF(3' Methylamino Phe) K | 60 |
| 61 | AcFRFFKNI | 61 |
| 62 | AcVRFFK(beta Ala)I | 62 |
| 63 | AcV(3'-amino-1'-carboxymethyl-pyridin-2'-one)FKNI | 63 |
| 64 | Ac(Idg)RFFKNI | 64 |
| 65 | AcAVRFFK | 65 |
| 66 | AcAVHFFKNI | 66 |
| 67 | AcV(2' Furanyl Ala)FFKNI | 67 |
| 68 | AcV(2' Thienyl Ala)FFKNI | 68 |
| 69 | AcVVKF(3' Cyano Phe)K | 69 |
| 70 | Ac(Phg)RFFKNI | 70 |
| 71 | AcIR(Tic)F(homo Pro) | 71 |
| 72 | AcLRFFKNI | 72 |
| 73 | AcVR(Phg)FKNI | 73 |
| 74 | AcVVRF(3' phenoxy Phe)K | 74 |
| 75 | AcVRF(Phg)KNI | 75 |
| 76 | AcVRFFK(beta Ala) | 76 |
| 77 | AcVVRFFK(beta Ala) | 77 |
| 78 | Ac(Chg)VRFFK | 78 |
| 79 | Ac(Chg)RF(4'-Indolyl Ala)KNI | 79 |
| 80 | AcVRF(3'-Carbazolyl Ala)KNI | 80 |
| 81 | Ac(Cpg)-NHNH(COCH$_2$CH(Ph)CO)KNI | 81 |
| 82 | AcVRF(3'-amino Phe)KNI | 82 |
| 83 | AcWRFFKNI | 83 |
| 84 | AcV(ω,ω dimethyl Lys)FFKNI | 84 |
| 85 | AcV(Chg)RFFK | 85 |
| 86 | AcV(nor Arg)FFKNI | 86 |
| 87 | AcVRF(3-Acetylamino Phe)KNI | 87 |
| 88 | Ac(Chg)R(Tic)F(4'-hydroxy Pro) | 88 |
| 89 | Ac(Chg)R(Tic) | 89 |
| 90 | AcVKFFENI | 90 |
| 91 | AcVRIFKNI | 91 |
| 92 | Ac(Cpg)-NHNH(COCH$_2$CH(Ph)CO)FKNI | 92 |
| 93 | Ac(Chg)R(Tic)-(3'-Carbazolyl Ala) | 93 |
| 94 | Ac(Chg)R(Tic)F(homo Pro) | 94 |
| 95 | Ac(Idg)R(Tic)FK | 95 |
| 96 | AcV(Idg)R(Tic)FK | 96 |
| 97 | AcV(Chg)R(Tic)F | 97 |
| 98 | AcV(Chg)RFFK | 98 |
| 99 | Ac(Chg)R(Tic)-(3'-Carbazolyl Ala)G | 99 |
| 100 | AcV(Chg)R(Tic)-(3'-Carbazolyl Ala)G | 100 |
| 101 | AcVVRF(3'-Acetylaminomethyl Phe) | 101 |
| 102 | AcVVRF(3'-Methylsulphonyl aminomethyl Phe) | 102 |
| 103 | (2,6-Dimethyl Benzoyl)-VRFFK | 103 |
| 104 | AcV(homo Arg)FFKNI | 104 |
| 105 | Ac(Cpg)-NHNH(COCH$_2$CH(Ph)CO)-(4'-Indolyl Ala)K | 105 |

Compounds in Table 3 can be assayed as the C-terminal amides using the assay protocol set forth in Section 5.4. Preferred compounds of the invention are those with $IC_{50}$ values of less than about 25 µM, less than about 10 µM, less than about 2.5 µM, less than about 1 µM, less than about 500 nM, less than about 250 nM, less than about 100 µM, less than about 50 nM, less than about 25 nM, less than about 10 µM, less than about 5 nM or less than about 1 nM using the assay protocol set forth in Section 5.4.

In one embodiment, the compounds of Table 3 contain all L residues.

In one embodiment, the compounds of Table 3 contain one or more, two or more, three or more, four or more, five or more, six or more, seven or more eight or more, or nine or more residues in the D configuration. In another embodiment, the compounds of Table 3 contain all D residues.

Also included within the scope of the present invention are "blocked" forms of the compounds of the invention, i.e., forms in which the N- and/or C-terminus is blocked with a moiety capable of reacting with the N-terminal —NH$_2$ or C-terminal —C(O)OH. In one embodiment, N-terminal blocking groups include RC(O)—, where R is —H, (C$_{1-6}$) alkyl, (C$_{-1-6}$) alkenyl, (C$_{1-6}$) alkynyl, (C$_{5-20}$) aryl, (C$_{6-26}$) alkaryl, 5-20 membered heteroaryl or 6-26 membered alkylheteroaryl. In a particular embodiment, N-terminal blocking groups include acetyl, formyl and dansyl. In one embodiment, C-terminal blocking groups include —C(O)NRR and —C(O)OR, where each R is independently defined as above. In a particular embodiment, C-terminal blocking groups include those where each R is independently methyl.

Preferred compounds of the invention are compounds of formulas I-IV that are resistant to cathepsin, particularly cathepsin B, D or L, degradation. In a preferred embodiment, the compounds of formulas I-IV have a half-life of greater than about 1 hour in a solution comprising cathepsin B, preferably greater than about 2 hours, more preferably greater than about 3 hours and most preferably greater than about 4 hours.

In another embodiment, the compounds of the invention, such as the compounds of formulas I-IV, are resistant to degradation by peptidases in vitro.

In another embodiment, the compounds of the invention, such as the compounds of formulas I-IV, are resistant to degradation in a cellular environment.

In another embodiment, the compounds of the invention, such as the compounds of formulas I-IV, are resistant to degradation by peptidases in vivo.

In another preferred embodiment, the compounds of the invention, including, but not limited to, the compounds of formulas I-IV, bind specifically to a MHC class II HLA-DR2 molecule, that is they have a higher affinity or preferentially bind to a MHC class II HLA-DR2 molecule. In another embodiment, the compounds of the invention, including those of formulas I-IV bind specifically to a MHC class II HLA-DR2 molecule, but do not bind to a MHC class II HLA-DR1 or MHC class II HLA-DR4 molecule. In a particular embodiment, the compounds of the invention, including, but not limited to, the compounds of formulas I-IV, have $IC_{50}$ values for a DR2 molecule which are about 0.5, about 0.1, about 0.01, about 0.001 or about 0.0001 of their $IC_{50}$ value for a DR1 or DR4 molecule.

In another embodiment, the compounds of the invention, including, but not limited to, the compounds of formulas I-IV, bind preferentially to DRB1*1501 over DRB5*0101. In a particular embodiment, the compounds of the invention, including, but not limited to, the compounds of formulas I-IV, have $IC_{50}$ values for DRB1*1501 which are about 0.5, about 0.1, about 0.01, about 0.001 or about 0.0001 of their $IC_{50}$ value for DRB5*0101.

Without being limited by any theory, in one embodiment the compounds of the invention, including, but not limited to, the compounds of formulas I-IV, competitively inhibit the binding of MBP to a MHC class II HLA-DR2 molecule.

It should be noted that if the stereochemistry of a structure or a portion of a structure is not indicated with, for example, bold or dashed lines, the structure or portion of the structure is to be interpreted as encompassing all stereoisomers of it.

4.3 Biological Assays

Without being limited by theory, the principle of antigen presentation is thought to require antigen binding by MHC class II molecules. In the example of multiple sclerosis, the MHC class II molecule, HLA-DR2 presents autoantigens derived from myelin that initiate T cell activation and destruction of the myelin nerve sheath. Accordingly, the binding affinity of the compounds of the invention to MHC class II HLA-DR molecules is one indicator of their usefulness as therapeutics for the treatment of an autoimmune disease. More specifically, inhibition of binding of MHC class II HLA-DR2 is an indicator of usefulness as a therapeutic for multiple sclerosis.

Assays useful for demonstrating the usefulness the compounds of the invention include those HLA molecule binding assays known in the art, such as Texier, C. et al. (2000) *J. Immunol.* 164:3177-3184; Jones, A. et al. (1999) *Bioorg. Med. Chem. Lett.* 9:2115-2118; Jones, A. et al. (1999) *Bioorg. Med. Chem. Lett.* 9:2109-2114; Wucherpfennig et al. (1994) *J. Exp. Med.* 179:279-290; and Bolin, D. R. et al. (2000) *J. Med. Chem.* 43:2135-2148, each of which is incorporated by reference herein in its entirety.

Assays useful for demonstrating the T cell proliferation inhibitory activity of the compounds of the invention include the assay set forth in Section 5.2 as well as those assays known in the art, such as Sarabu, R. (2002) *Drug. Des. Disc.* 18:3-7; Bolin, D., (2000) *J. Med. Chem.* 43:2135-2148; Chirathaworn, C. (2002) *J. Immunol.* 168(11):5530-5537; Falcioni, F., et. al. (1999) *Nature Biotechnology* 17:562-567, each of which is incorporated by reference herein in its entirety.

Animal models useful for demonstrating the therapeutic utility of the compounds of the invention include those known in the art, such as Vallabhapurapu, S. (2001) *Eur. J. Immunol.* 31:2612-2622 and U.S. Pat. No. 5,833,987, each of which is incorporated by reference herein in its entirety.

Assays useful for demonstrating stability of the compounds of the invention to cathepsin degradation include those known in the art, such as Li, M. (1993) *Bioconjug. Chem.* 4:275-83 and Nakagomi, K. (2002) *Biol. Pharm. Bull.* 25:564-8.

4.4 Synthesis and Preparation

The compounds of the invention can generally be prepared via solid-phase synthesis procedures such as those described in Barany, G. and Merrifield, R. B. *The Peptides*, Gross E., Meienhofer, J. Eds., Academic Press: New York, 1980, vol. 2, pp. 1-284; *Solid phase synthesis: A practical guide*, S. A. Kates, F. Albericio, Eds. Marcel Dekker: New York, 2000; Myers A. G. et al. (1997) *J.Amer.Chem.Soc.* 119:656; Myers A. G. et al. (1999) *J. Org. Chem.* 64:3322D; A. Wellings, E. Atherton, (1997) *Methods Enzymol.* 289:44; Fields, G. B. et al., (1990) *Int. J. Peptide Protein Res.* 35:161; H. Rink, (1987) *Tetrahedron Lett.* 28: 3787; R. C. Sheppard, B. J. Williams, (1982) *Int. J. Rept. Protein Res.* 20:451; J. Coste, et al., (1991) *Tetrahedron Lett.* 32:1967; L. A. Carpino, A. Elfaham, C. A. Minor, F. Albericio, (1994) *J. Chem, Soc. Chem. Comm.*, 201; M. Felix, et al., (1998) *J. Peptide Res.* 52:155; U.S. Pat. No. 5,770,732 issued Jun. 23, 1998; U.S. Pat. No. 5,514,814 issued May 7, 1996; and U.S. Pat. No. 5,489,692 issued Feb. 6, 1996, which are incorporated by reference herein in their entirety.

Some convenient methods are illustrated in Schemes 1-4. Starting materials useful for preparing the compounds of the invention, and intermediates therefore, are commercially available or can be prepared from commercially available materials using known synthetic methods and reagents.

In general, amino acids (natural, non-natural, or peptide mimetics) are protected as N-Fmoc derivatives with acid-labile protecting groups as appropriate on reactive side chain substituents. Fmoc-Rink or Knorr linker-BHA resin is used for the synthesis of C-terminal amides. TGT-alcohol resin is used for the synthesis of C-terminal acids. Fmoc groups are removed using 20-40% piperidine in DMF. Condensation of the appropriate N-Fmoc amino acid is accomplished using HBTU/N-methyl morpholine in DMF (the HOBT active ester of the amino acid is preformed and added to the resin). Couplings to N-alkyl or imino acids are performed with either BOP-Cl or PyBrOP in NMP. After deprotection of the Fmoc group using 20-40% piperidine in DMF, coupling of the next N-Fmoc amino acid or capping group is accomplished in the same manner. This cycle is repeated until the desired sequence has been synthesized on the resin.

Final deprotection of the N-terminal Fmoc group, if present, is followed by treatment with an acid anhydride, activated carboxylic acid or sulfonic acid in DMF for 1 hour. When C-terminal amides are desired, the resin is washed with DMF, ethanol, methylene chloride and dried in vacuo. The linear compounds are cleaved from the resin and any side chain protecting groups are removed by treatment with a 80% solution of TFA in dichloromethane, with the addition of water (5%) and triisopropylsilane (5%). Filtrates are concentrated in vacuo, and diluted with diethyl ether to afford crude compounds as white solids. Crude products are purified by reverse phase HPLC (C18 silica gel; acetonitrile/water/TFA gradient elution) and lyophilized to give the final compounds. When the sequence includes a basic substitutent, such as an amino group of a lysine, the product may be formed as a TFA salt. If desired, the TFA salt can be exchanged for another pharmaceutically acceptable salt by neutralization and treatment with a pharmaceutically acceptable acid to form a new salt.

The final products can be characterized by analytical HPLC, FAB-MS, ES-MS and/or amino acid analysis. HPLC purity, as determined from all UV active peaks, is typically greater than 97%.

Non-natural, non-alpha amino acids and peptide mimetics are incorporated into sequences by the same methodology and, if required, the couplings are followed by detection of any unreacted free amino terminus using a standard Kaiser test. In such instances couplings are repeated until a negative Kaiser test is obtained.

When C-terminal groups other than amide are desired, the synthesis is carried out on TGT-alcohol resin as described above, except that the side chain-protected compound is cleaved from the resin with 2% TFA to release a protected compound carboxylic acid, which can in a separate step be amidated or converted to an ester or sugar derivative and subsequently deprotected as described above.

Compounds of Formulas I-IV can be synthesized using the synthesis depicted in Schemes 1-7, below.

Schemes 1a and 1b: Preparation of Chiral α Amino Acid

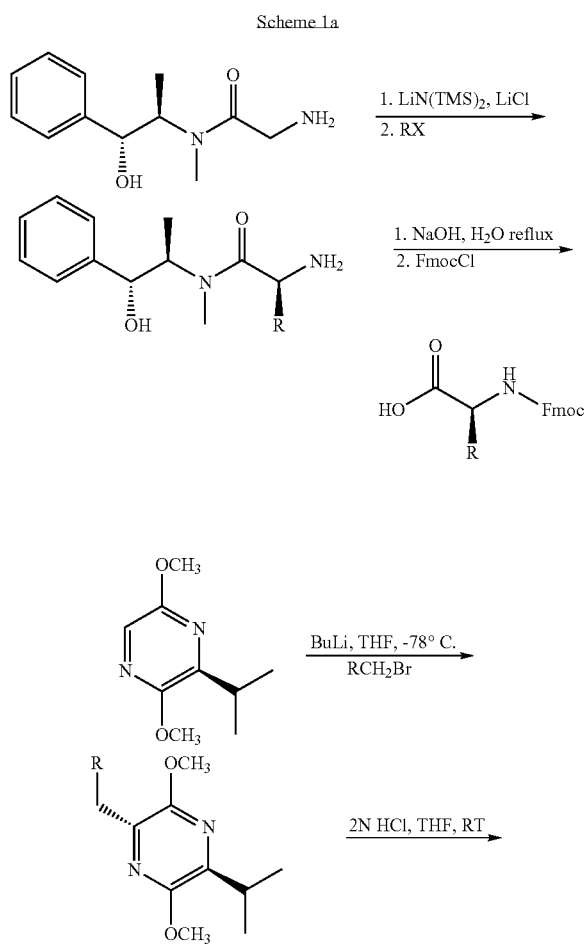

-continued

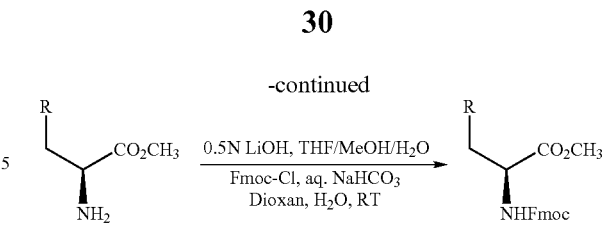

Scheme 2:
Preparation of Carbazole Alanine Building Block

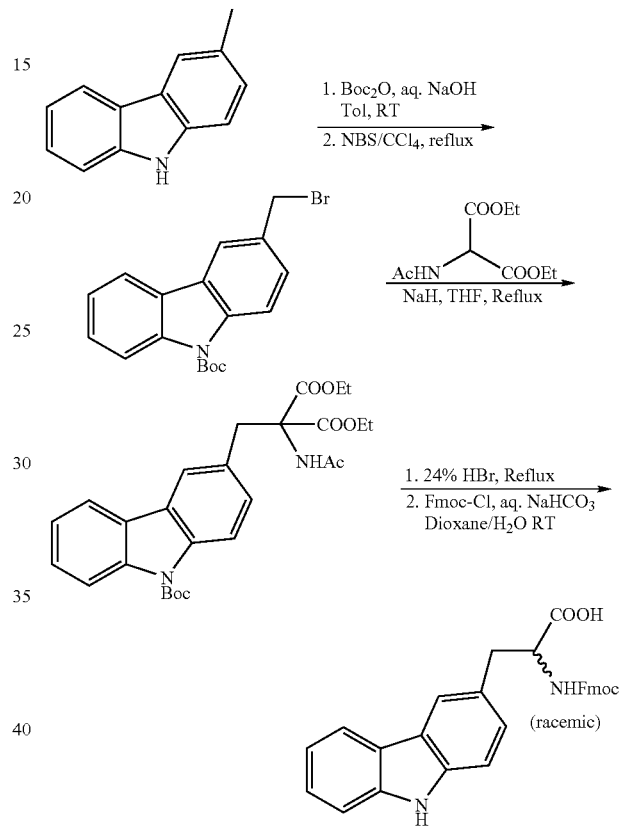

N-Boc 3 Methylcarbazole

To a solution of 3-methylcarbazole (500 mg, 2.76 mmol) in toluene (7.5 mL), was added sodium hydroxide (5 g, 125 mmol) as a solution in water (15 mL) followed by tri n-butyl benzyl ammonium chloride (25 mg). The two-phase solution was stirred at about 0° C. and di t-butylcarbonate (1.25 g, 5.7 mmol) was added in one portion. The mixture was stirred for about 1 h at about 0° C., the toluene layer was separated and the aqueous layer was extracted with ethyl acetate (2×10 mL). The combined organic layers were washed with water (2×10 mL); dried (MgSO$_4$) and concentrated under in vacuo to afford the crude product (725 mg, 96% yield). ES-MS (M+H)$^+$ 282.0 (calc. 282.1).

N-Boc 3 Bromomethylcarbazole

To a stirred solution of N-Boc 3-Methylcarbazole (85 mg, 0.3 mmol) and N-bromo succinimde (54 mg, 0.3 mmol) in carbon tetrachloride (10 mL) was added benzoyl peroxide (10 mg), and the reaction was heated at reflux for about 12 h. The cooled reaction mixture was filtered through celite, the solvent was removed under reduced pressure and the crude product was purified using column chromatography on silica gel with hexane/ethyl acetate as eluant (86 mg, 80% yield). ES-MS (M−Br)$^+$ 280.9 (calc. 280.15).

2-Acetylamino-2-(9-tert-butoxycarbonyl-9H-carbazol-3-yl-methyl)-malonic acid diethyl ester To a stirred suspension of sodium hydride (100 mg of a 60% dispersion in oil, 2.5 mmol) in THF (10 mL) at about 0° C. under an atmosphere of argon, was added dropwise a solution of acetamido diethyl malonate (241 mg, 1.1 mmol) in THF (1 mL). The stirred reaction mixture was allowed to warm to room temperature over about 30 minutes, cooled to about 0° C. and a solution of N-Boc 3-bromomethylcarbazole (400 mg, 1.1 mmol) in THF (2 mL) was added. The stirred reaction mixture was heated at about 60° C. for about 6 h. The cooled reaction mixture was quenched with brine (10 mL), and extracted with ethyl acetate (3×20 mL). The combined organic extracts were washed with water (10 mL), dried (MgSO4) and solvent was removed in vacuo. The crude product was purified using column chromatography on silica gel with 1:1 hexane/ethyl acetate as eluant to afford the product (150 mg, 27% yield). ES-MS (M+H)$^+$ 497.3 (calc. 497.2).

2-Amino-3-(9H-carbazol-3-yl)-propionic acid

2-Acetylamino-2-(9-tert-butoxycarbonyl-9H-carbazol-3-ylmethyl)-malonic acid diethyl ester (200 mg, 0.4 mmol) was combined with hydrogen bromide (4 mL of a 24% aqueous solution) and refluxed for about 12 h. The cooled reaction mixture was evaporated under reduced pressure and dried under high vacuum to afford the amino acid as the hydrogen bromide salt. ES-MS (M+H)$^+$ 255.0 (calc. 254.1).

rac-3-(9H-Carbazol-3-yl)-2-(9H-fluoren-9-ylmethoxycarbonylamino)-propionic acid

Crude 2-Amino-3-(9H-carbazol-3-yl)-propionic acid HBr salt (50 mg, 0.15 mmol) was combined with aqueous sodium hydrogen carbonate (2 mL of a saturated solution) and dioxane (2 mL) and stirred at about 0° C. 9-Fluorenylmethyl chloroformate (100 mg, 0.39 mmol) was added and the reaction stirred at room temperature for about 8 h. The reaction mixture was diluted with water (25 mL), and extracted with diethyl ether (2×25 mL). The aqueous layer was acidified with hydrochloric acid to pH 3, and extracted with ethyl acetate (3×25 mL). The combined ethyl acetate extracts were concentrated under reduced pressure and dried in vacuo. The crude product was purified using column chromatography on silica gel with 10% methanol in dichloromethane as eluant to afford rac-3-(9H-Carbazol-3-yl)-2-(9H-fluoren-9-yl-methoxycarbonylamino)-propionic acid (ES-MS (M+H)$^+$ 477.2 (calc. 477.17)), which was utilized directly in the synthesis of peptide analogs by solid phase peptide synthesis protocols.

Scheme 3:
Incorporation of Non-Natural Amino Acids

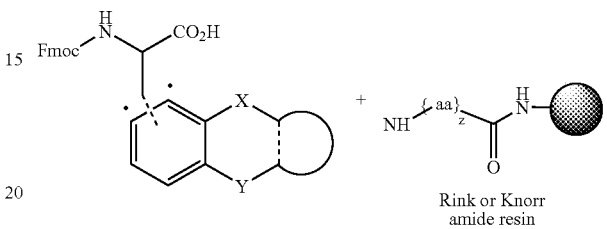

Rink or Knorr amide resin

1. HBTU, NMe Morpholine (SPS)
2. Piperidine/DMF
3. Fmoc-aa-CO$_2$H, HBTU, NMe Morpholine
4. Repeat cycles 2 & 3 as necessary
5. Piperidine, R'CO$_2$H, HBTU, NMe Morpholine
6. TFA cleavage from resin/deprotect side chains

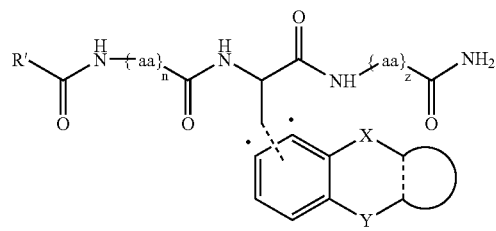

aa = amino acid (natural/unatural) or linear peptide

Scheme 4:
Preparation of Diacyl Hydrazide Linked Peptide Analogs

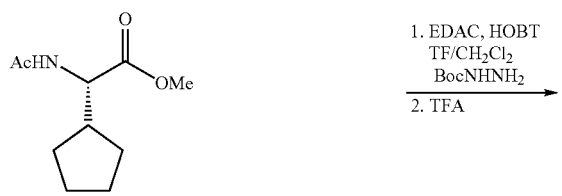

1. EDAC, HOBT TF/CH$_2$Cl$_2$ BocNHNH$_2$
2. TFA

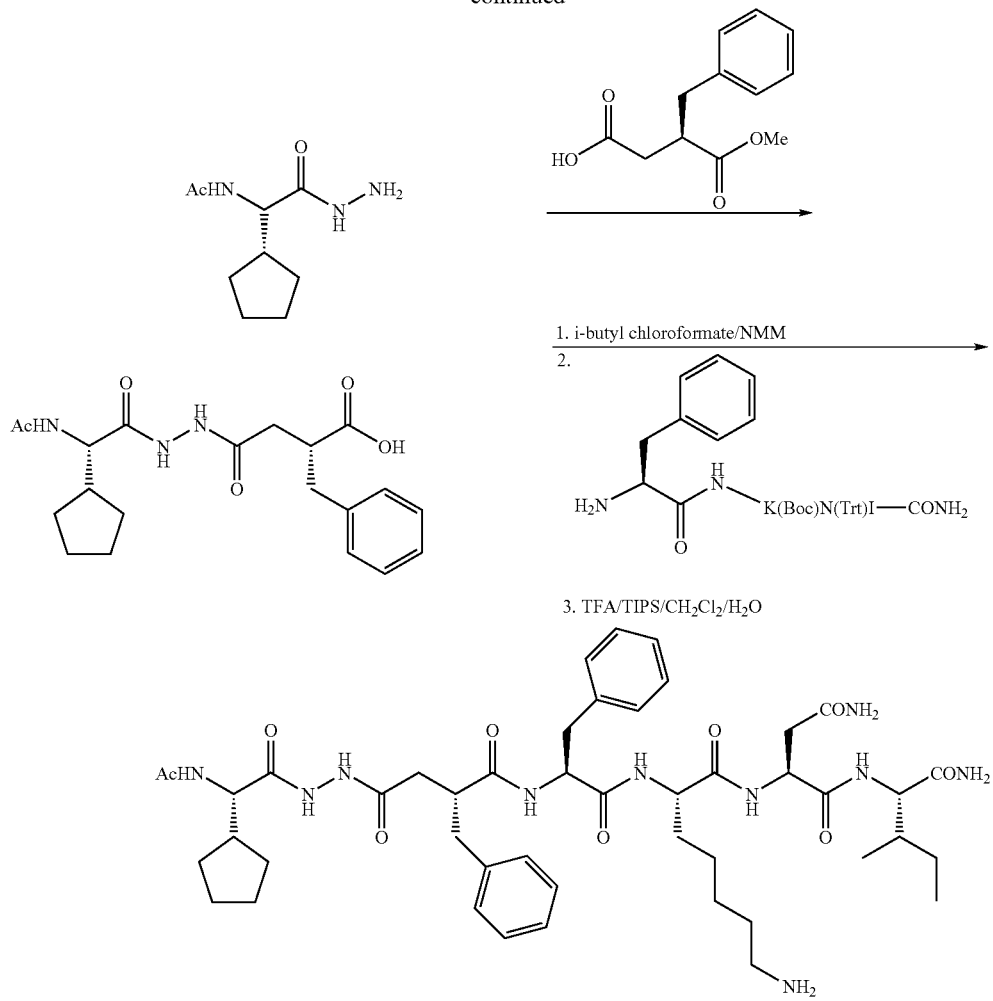

N'-Boc (N-Acetyl Cyclopentylglycinyl) Hydrazide (S)-N-Acetyl cyclopentylglycine (450 mg, 2.4 mmol) was combined with 1-hydroxy benztriazole hydrate (371 mg, 2.4 mmol), 1-ethyl-3-(3-dimethylamino propyl) carbodiimide hydrochloride (465 mg, 2.4 mmol) and N-Boc hydrazine (327 mgs, 2.4 mmol) in dry THF (10 mL)/dichloromethane (10 mL) and stirred at room temperature under an atmosphere of argon for about 18 h. The reaction mixture was concentrated at reduced pressure, diluted with dichloromethane (50 mL) and washed with aqueous sodium hydrogen carbonate (25 mL of a saturated solution); brine (25 mL) and dried (Na$_2$SO$_4$). The solution was filtered through a plug of silica gel, and the silica was washed with ethyl acetate (150 mL). The combined solvent extracts were concentrated at reduced pressure, and the residue recrystalised from ethyl acetate (338 mg, 47% yield).

N-Acetyl Cyclopentylglycinyl Hydrazide

To a suspension of N'-Boc-(N-Acetyl Cyclopentylglycinyl) Hydrazide (445 mg, 1.5 mmol) in dichloromethane (25 mL) was added a solution of TFA (10 mL) in dichloromethane (10 mL) and reaction stirred for about 3 h at room temperature. The reaction mixture was concentrated at reduced pressure, diluted with dichloromethane (20 mL) and concentrated. This was repeated two more times to remove all the TFA, and the residue dried in vacuo. The residue was triturated with dry diethyl ether and the resultant solid collected and dried in vacuo (374 mg, 80% yield).

3-[N'-(Acetylamino-cyclopentyl-acetyl)-hydrazinocarbonyl]-2-benzyl-propionic acid methyl ester (R)-2-Benzyl succinic acid methyl ester (326 mg, 1.4 mmol) was combined with HBTU (584 mg, 1.54 mmol), N-methylmorpholine (170 µL, 1.54 mmol) in dry DMF (5 mL) with stirring under an atmosphere of argon. After about 40 min (R)-N-Acetyl cyclopentylglycine hydrazide (437 mg, 1.4 mmol) and N-methylmorpholine (340 µL, 3.1 mmol) were added and reaction stirred at room temperature overnight. The reaction mixture was concentrated in vacuo and the residue was partitioned between water (25 mL) and ethyl acetate (80 mL). The organic phase was separated and the aqueous layer was extracted with ethyl acetate (2×25 mL). The combined ethyl acetate extracts were washed with cold aqueous citric acid (20 mL of a 5% solution), cold aqueous sodium hydrogen carbonate (20 mL of a saturated solution) and dried (Na$_2$SO$_4$). The solvent was removed at reduced pressure to afford the crude diacyl hydrazide (426 mg, 76% yield), which was used in the next step without further purification.

3-[N'-(Acetylamino-cyclopentyl-acetyl)-hydrazinocarbonyl]-2-benzyl-propionic acid To a stirred solution of 3-[N'-(Acetylamino-cyclopentyl-acetyl)-hydrazinocarbonyl]-2-benzyl-propionic acid methyl ester (510 mg, 1.26 mmol) in methanol (30 mL) was added a solution of lithium hydroxide (252 mg, 6 mmol) in water (0.5 mL). Reaction was stirred at room temperature for about 3 h, concentrated in vacuo, and the remaining slurry was diluted with water (2 mL) and acidified to pH 3 with 6M hydrochloric acid. Sufficient acetonitrile was added to dissolve all the solids and the solution lyophilized to afford a white solid. The product was isolated by reverse phase HPLC on C18 silica gel by gradient elution with acetonitrile/water/TFA (0.075%), 132.5 mg, 27%.

Scheme 5:
Key mono- and di-pyrrolinone intermediates

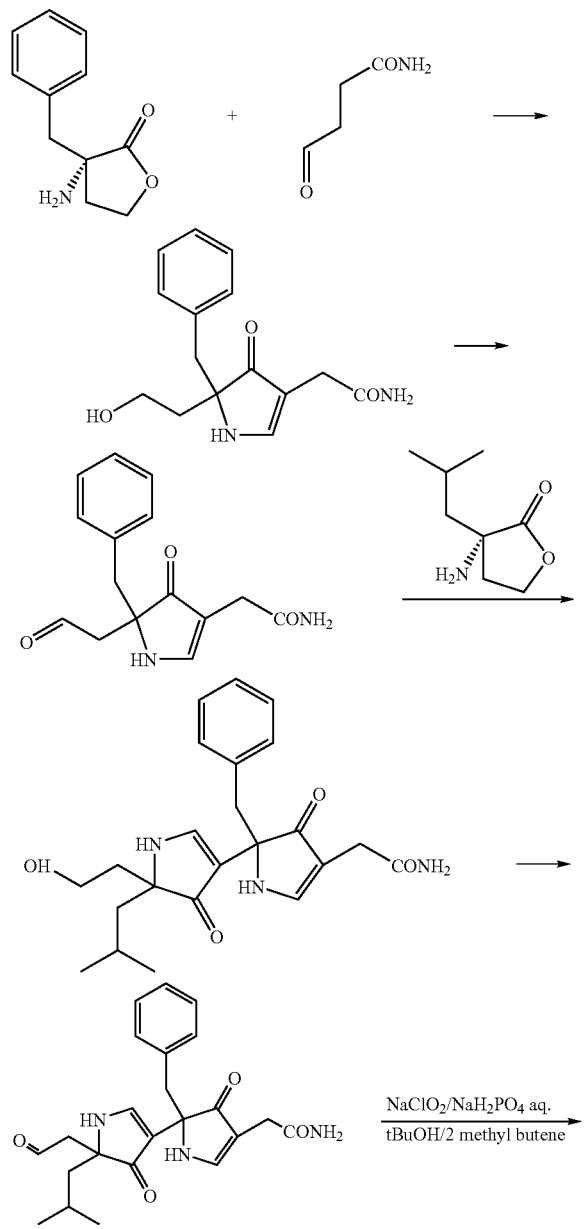

-continued

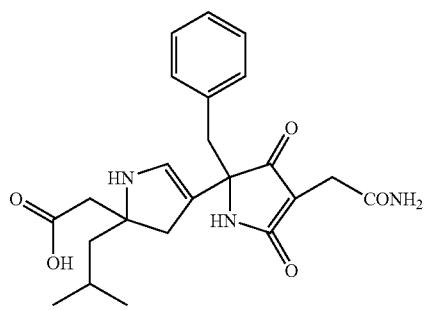

REFERENCES (i) A. B. Smith III, R. F. Hirschmann, H. Liu and H. Ikumura, New Solution and solid phase synthesis of pyrrolinones and polypyrrolinones., US Patent Application 200220133027, 2002.

(ii) A. B. Smith III, H. Liu and R. F. Hirschmann, Organic Letters, 2000, 2(14), 2037.

(iii) A. B. Smith III, H. Liu, H. Okamura, D. A. Favor and R. F. Hirschmann, Organic Letters, 2000, 2(14), 2041.

Scheme 6:
Preparation of Dipyrrolinones

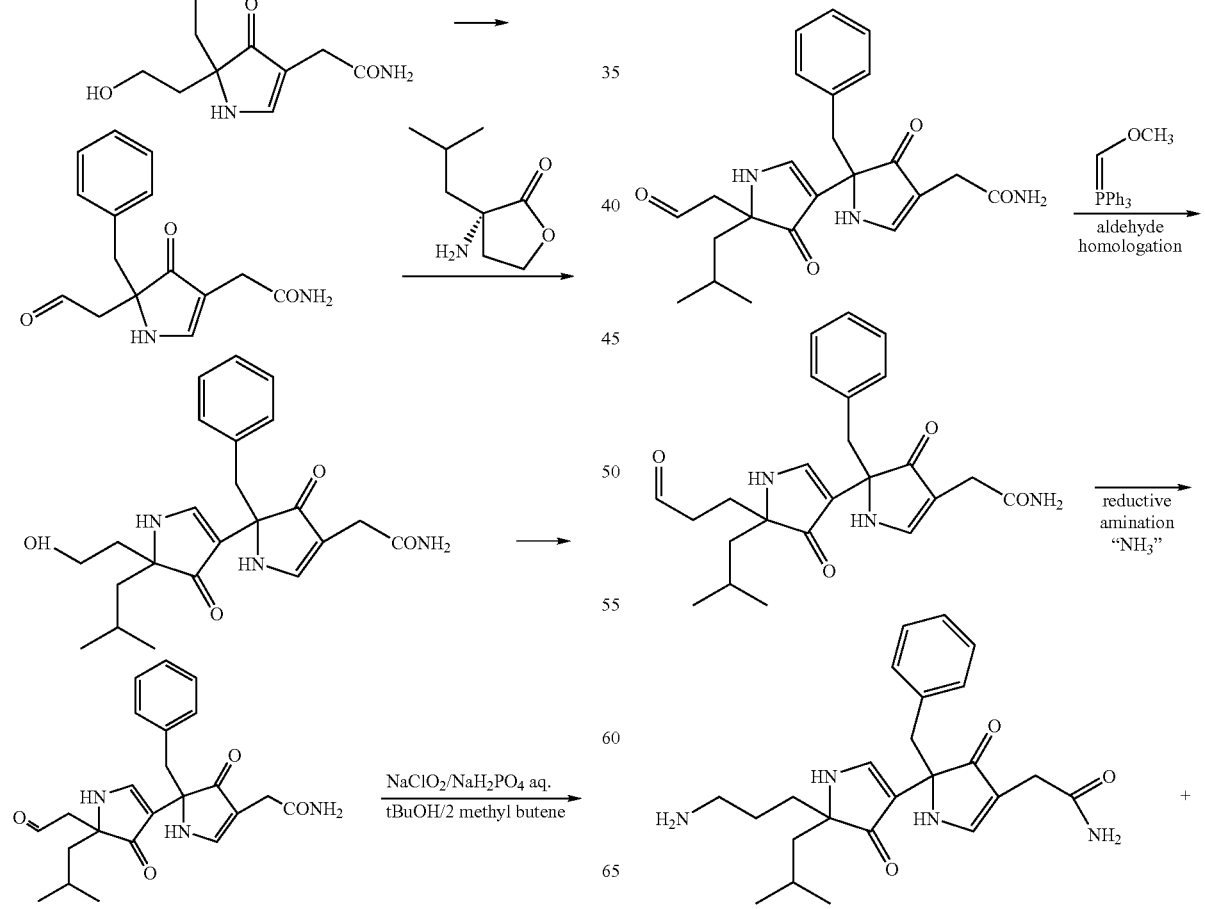

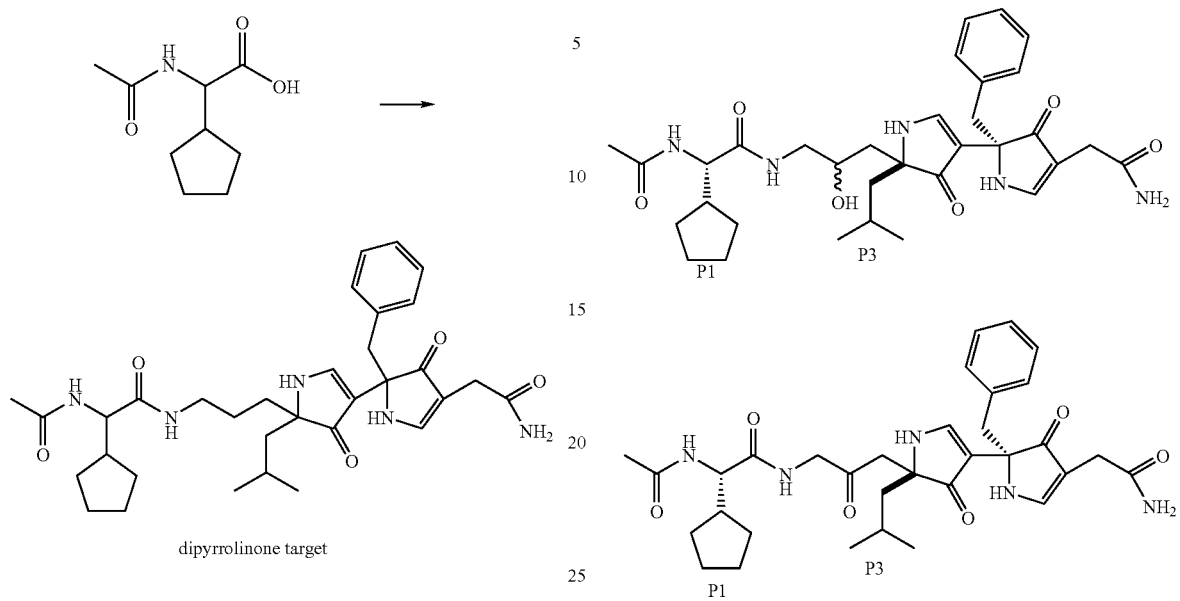

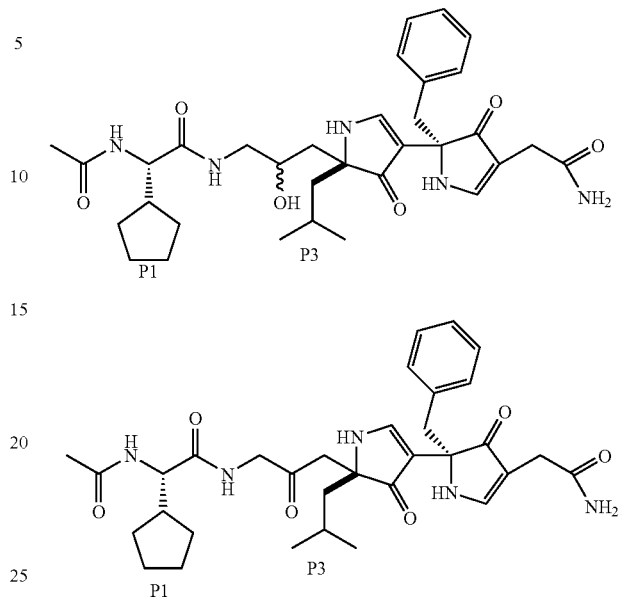

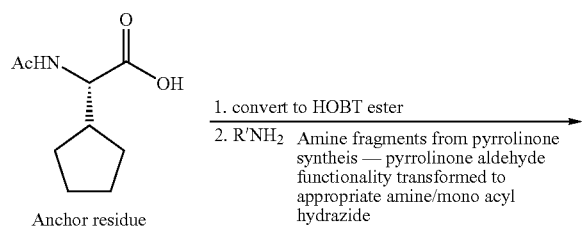

Scheme 7:
Preparation of Dipyrrolinones

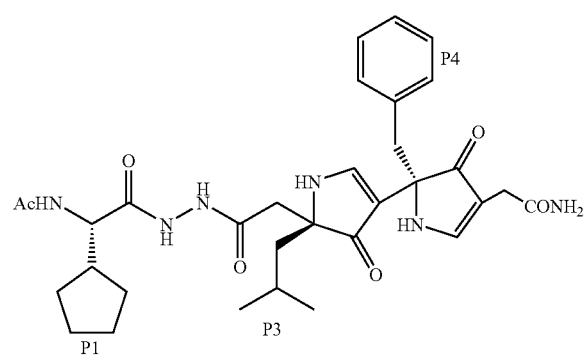

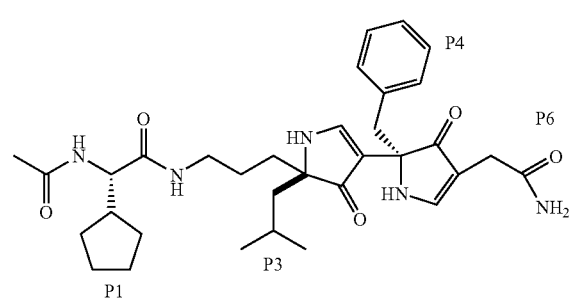

4.5 Methods of Use

A first embodiment of the invention relates to a method for inhibiting antigen binding to a MHC class II molecule in vitro or in vivo, particularly a MHC class II HLA-DR1, MHC class II HLA-DR2 or MHC class II HLA-DR4 molecule comprising contacting a cell, such as a mammalian cell, with an effective amount of a compound of the invention. In a preferred embodiment, the MHC class II HLA-DR molecule is a MHC class II HLA-DR2 molecule. In one embodiment, the compound of the invention competitively inhibits an antigen associated with an autoimmune disease from binding to a MHC class II HLA-DR molecule, including MBP, the antigen associated with binding to HLA-DR2 in multiple sclerosis.

In another embodiment, the invention relates to a method for inhibiting antigen presentation by a MHC class II HLA-DR molecule in vitro or in vivo, particularly a MHC class II HLA-DR1, MHC class II HLA-DR2 or MHC class II HLA-DR4 molecule comprising contacting a cell, such as a mammalian cell, with an effective amount of a compound of the invention. In a preferred embodiment, the MHC class II HLA-DR molecule is a MHC class II HLA-DR2 molecule.

In another embodiment, the invention relates to a method for inhibiting T cell proliferation in vitro or in vivo comprising contacting a cell, such as a mammalian cell, with an effective amount of a compound of the invention.

In another embodiment, the invention relates to a method for treating or preventing a disease treatable or preventable by inhibiting T cell proliferation in vivo comprising contacting a cell, such as a mammalian cell, with an effective amount of a compound of the invention.

The present invention further encompasses the incorporation of a compound of the invention into pharmaceutical compositions and single unit dosage forms useful in the treatment and prevention of a variety of diseases and disorders. Specific diseases and disorders include those responsive to the inhibition of antigen binding to a MHC class II HLA-DR molecule, those responsive to the inhibition of antigen presentation by a MHC class II HLA-DR molecule and those responsive to the inhibition of T cell proliferation. In a preferred embodiment, the MHC class II HLA-DR molecule is a MHC class II HLA-DR2 molecule.

In one embodiment, the invention relates to a method for treating or preventing a disease responsive to the inhibition of antigen binding to a MHC class II HLA-DR molecule, particularly a MHC class II HLA-DR1, MHC class II HLA-DR2 or MHC class II HLA-DR4 molecule, comprising administering an effective amount of a compound of the invention to a patient in need thereof. In a preferred embodiment, the MHC class II HLA-DR molecule is a MHC class II HLA-DR2 molecule.

In another embodiment, the invention relates to a method for treating or preventing a disease responsive to the inhibition of antigen presentation by a MHC class II HLA-DR molecule, particularly a MHC class II HLA-DR1, MHC class II HLA-DR2 or MHC class II HLA-DR4 molecule, comprising administering an effective amount of a compound of the invention to a patient in need thereof. In a preferred embodiment, the MHC class II HLA-DR molecule is a MHC class II HLA-DR2 molecule.

In another embodiment, the invention relates to a method for treating or preventing a disease responsive to the inhibition of T cell proliferation comprising administering an effective amount of a compound of the invention to a patient in need thereof. Particular diseases which the compounds of the invention are useful for treating or preventing include, but are not limited to: a genetic disease, a central nervous system ("CNS") disease, an inflammatory disease, a neurodegenerative disease or an autoimmune disease.

In one embodiment, the disease is multiple sclerosis, which both a genetic disease and an autoimmune disease.

In another embodiment, the genetic disease is diabetes. In one embodiment, the diabetes is Type I diabetes, diabetes mellitus or juvenile diabetes.

Autoimmune diseases include those that affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune diseases include, but are not limited to, encephalomyelitis, oophoritis, graft versus host disease, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue disease, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo and Wegener's granulomatosis. Thus, the invention encompasses the use of compounds of the invention to treat the diseases described above and herein.

In one embodiment, the patient undergoes or has undergone a genetic screening process to determine the MHC class II allele that the patient has. In a particular embodiment, it has been determined that the patient has the MHC class II HLA-DR2 allele.

In another embodiment, the patient has been diagnosed as having multiple sclerosis or symptoms of multiple sclerosis.

In another embodiment, the patient undergoes or has undergone a screening process to determine the presence of a cell in which normal cellular proteins are recognized as foreign, comprising the steps of screening a patient or a cell extracted therefrom by an acceptable T cell proliferation assay.

Specific methods of the invention further comprise the administration of an additional therapeutic agent (i.e., a therapeutic agent other than a compound of the invention). In certain embodiments of the present invention, a compound of the invention can be used in combination with at least one other therapeutic agent.

In particular, the invention provides combination therapies for prevention, treatment or amelioration of one or more symptoms associated with an autoimmune disease in a patient, said combination therapies comprising administering to said a compound of the invention, and at least one other prophylactic or therapeutic agent which has a different mechanism of action than the compound of the invention.

Therapeutic agents include, but are not limited to immunomodulatory agents, T cell receptor modulators, β-interferons, non-opioid analgesics, non-steroid anti-inflammatory agents, antiemetics, β-adrenergic blockers, anticonvulsants, antidepressants, Ca2+-channel blockers, anticancer agent or mixtures thereof.

Examples of immunomodulatory agents include, but are not limited to, methothrexate, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), Copaxone® (glatiramer acetate). T cell receptor modulators, and cytokine receptor modulators.

Examples of T cell receptor modulators include, but are not limited to, anti-T cell receptor antibodies (e.g., anti-CD4 monoclonal antibodies, anti-CD3 monoclonal antibodies, anti-CD8 monoclonal antibodies, anti-CD40 ligand monoclonal antibodies, anti-CD2 monoclonal antibodies) and CTLA4-immunoglobulin.

Examples of β-interferons include, but are not limited to, Avonex® (interferon β-1a), Betaseron® (interferon β-1b) and Rebif® (interferon β-1a).

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. The prophylactic or therapeutic agents of the combination therapies of the present invention can be administered concomitantly or sequentially to a patient. The prophylactic or therapeutic agents of the combination therapies of the present invention can also be cyclically administered. Cycling therapy involves the administration of a first prophylactic or therapeutic agent for a period of time, followed by the administration of a second prophylactic or therapeutic agent for a period of time and repeating this sequential administration, i.e., the cycle, in order to reduce the development of resistance to one of the agents, to avoid or reduce the side effects of one of the agents, and/or to improve the efficacy of the treatment.

The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors.

In general, the recommended daily dose range for the conditions described herein lie within the range of from about 0.1 mg to about 3000 mg per day, given as a single once-a-day dose or as divided doses throughout a day. More specifically, the daily dose is administered in a single dose or in equally divided doses. Specifically, a daily dose range should be from about 1 mg to about 2500 mg per day, more specifically between about 10 mg and about 2000 mg per day, more specifically between about 50 mg and about 1500 mg per day, or as necessary to achieve effective concentrations at the site of action sufficient to block antigen presentation. This dose depends on the route of administration, bioavailability, metabolic stability, protein binding, and other factors known in the art. Compounds may also be administered in long-acting depot formulations that release effective amounts of the active ingredient over periods of several days to several weeks or months; usually following intramuscular or subcutaneous administration. In managing the patient, the therapy should be initiated at a lower dose, at about 1 mg per day to about 25 mg per day, and increased if necessary up to about 200 mg per day to about 1000 mg per day, or to about 1500 mg per day to about 3000 mg per day, as either a single dose or divided doses, depending on the patient's global response.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

4.6 Pharmaceutical Compositions

Pharmaceutical compositions and single unit dosage forms comprising a compound of the invention, or a pharmaceutically acceptable prodrug, salt, solvate or hydrate thereof, are also encompassed by the invention and methods of use disclosed herein. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Pharmaceutical compositions and dosage forms of the invention comprise a compound of the invention, or a pharmaceutically acceptable prodrug, salt, solvate or hydrate thereof. Pharmaceutical compositions and dosage forms of the invention typically also comprise one or more pharmaceutically acceptable excipients.

A particular pharmaceutical composition encompassed by this embodiment comprises a compound of the invention, or a pharmaceutically acceptable prodrug, salt, solvate or hydrate thereof, and at least one additional therapeutic agent. Examples of additional therapeutic agents include, but are not limited to: immune suppressor agents, anti-cancer drugs and anti-inflammation therapies.

Single unit dosage forms of the invention are suitable for oral, mucosal (e.g., nasal, inhalation, sublingual, vaginal, buccal, or rectal), parenteral (e.g., subcutaneous, intravenous, bolus injection, infusion, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

In one embodiment, the compound of the invention is administered in a pharmaceutical formulation comprising carbonate.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of the invention, or a pharmaceutically acceptable prodrug, salt, solvate or hydrate thereof lie within the range of from about 0.1 mg to about 3000 mg per day, given as a single once-a-day dose in the morning but preferably as divided doses throughout the day taken with food. More specifically, the daily dose is administered twice daily in equally divided doses. Specifically, a daily dose range should be from about 1 mg to about 2500 mg per day, more specifically, between about 10 mg and about 2000 mg per day,more specifically, between about 25 mg and about 1500 mg per day,more specifically, between about 50 mg and about 1000 mg per day, more specifically, between about 100 mg and about 750 mg per day, more specifically, between about 200 mg and about 500 mg per day, more specifically, between about 250 mg and about 300 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response.

In one embodiment, the compounds of the invention are administered in a pharmaceutical composition comprising liposomes. The liposomes may be polymerized or unpolymerized and the compound of the invention may optionally be intercalated within the liposomes. Suitable lipophilic solvents or vehicles include fatty oils such as sesame oil, or synthetic fatty acid esters, such as ethyl oleate or triglycerides.

4.6.1. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein, such as organic solvents including propylene glycol, polyethylene glycol, ethanol, glycerol, polyethylene glycol ricinoleate (Cremophor) or polyoxyethylene sorbitan fatty acid esters (Tween), can also be incorporated into the parenteral dosage forms of the invention. Parenteral solutions of the compounds of the invention can also comprise human serum proteins which serve as crystallization inhibitors, such as those described in U.S. Pat. No. 4,842,856, incorporated by referene herein in its entirety. Parenteral solutions of the compounds of the invention can further comprise poloxamers or polysorbates.

Parenteral dosage forms can also be administered in depot, long acting or slow-release forms comprising a compound of the invention in a matrix of a polymer of polyols and hydroxy carboxylic acids such as those disclosed in International Publication WO 78/0001 1, incorporated herein by reference in its entirety. Depot forms can also comprise a polyol ester containing polymeric-dicarboxylic acid residues (e.g. tartaric acid) such as those described in U.S. Pat. Nos. 5,922,682 and 5,922,338, each of which is incorporated herein by reference in its entirety. Additional depot forms include matrices comprised of an ester of polyvinyl alcohol (M.W. of about 14000), polyethylene glycol (M.W. of about 6000 to 20,000) or polymer hydroxycarboxylic ester residues (e.g., lactic acid M.W. of about 26,000 to 114,000) or glycolic acid (M.W. of about 10,000), such as those disclosed in European application No. 92918, incorporated herein by reference in its entirety. Delayed release formulations for parenteral dosase forms also include binder-free granules as disclosed in U.S. Pat. No. 4,902,516 and those disclosed for use with vitamin D in U.S. Pat. No. 5,795,882, each incorporated by reference herein in its entirety.

Further parenteral dosage forms include wax microspheres such as those disclosed in U.S. Pat. No. 6,340,671, lipophilic formulations such as those disclosed in U.S. Pat. No. 6,335,346, non-acqueous compositions such as those disclosed in U.S. Pat. No. 5,965,603, carbohydrate polymers such as those disclosed in U.S. Pat. No. 5,456,922 and emulsions such as those disclosed in U.S. Pat. Nos. 4,563,354 and 5,244,925, each incorporated by reference herein in its entirety.

Parenteral dosages can be delivered via implantable devices, osmotic pumps, or catheter systems which are capable of delivering the composition at selectable rates (See U.S. Pat. Nos. 6,471,688; 6,436,091; 6,413,239; 6,464,688; 5,672,167; and 4,968,507, each incorporated by reference herein in its entirety).

4.6.2. Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990) or *Remington: The Science and Practice of Pharmacy*, 20th ed., Lippincott, Williams and Wilkins, (2000).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.6.3. Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, carboxymethyl cellulose, or other polymer matrices, gels, permeable membranes, osmotic systems, multilayer coatings, microparticles, liposomes, microspheres, or a combination thereof to provide the desired release profile in varying proportions. In a preferred embodiment, the controlled-release formulation is biodegradable. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release. The compound of the invention may also be administered in a depot formulation or inclusion complex and can optionally be inserted under the skin.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.6.4 Transdermal Topical and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5. EXAMPLES 5.1. Synthesis of Compound 92 (Ac(Cpg)NHNH [COCH$_2$CH(Ph)CO]FKNI) (SEQ ID NO.: 92)

NH$_2$-Phe-Lys(N'-Boc)-Asn(Trt)-Ileu-NH$_2$ (SEQ ID NO.: 109) was prepared by Fmoc synthesis protocols on Sieber amide resin and cleavage with 1% TFA in dichloromethane (Boc and trityl side chain protection remained intact under these conditions). The protected peptide was purified by gradient elution on a reverse phase HPLC C18 silica gel column with acetonitrile/water/TFA (0.075%). Fractions containing the pure peptide were concentrated at reduced pressure and lyophilized to afford the peptide (TFA salts of basic groups) as a fine powder.

To a stirred solution of 3-[N'-(Acetylamino-cyclopentyl-acetyl)-hydrazinocarbonyl]-2-benzyl-propionic acid (49 mgs, 0.13 mmol) in dry THF (1.5 mL) and DMF (1 mL) at 0° C. was added N methyl morpholine (17 μL, 0.15 mmol) followed by isobutyl chloroformate (19 μL, 0.14 mmol). Reaction was stirred at 0° C. for 30 min, and a solution of NH$_2$-Phe-Lys(N'-Boc)-Asn(Trt)-Ileu-NH$_2$ (101 mgs, 0.12 mmol) in dry THF (1 mL) and DMF (1 mL) was added in one portion. Reaction was allowed to attain RT and stirred for 12 h. The reaction mixture was concentrated at reduced pressure and the residue combined with TFA/dichloromethane/tri-isopropylsilane/water (5 mL of a 5:4:0.5:0.5 mixture) at RT for 20 min to effect global deprotection of the crude product. The solvent was removed at reduced pressure, diluted with dichloromethane (50 mL) and concentrated. This was repeated two more times to remove all the TFA, and the residue dried under vacuum. The residue was triturated with dry diethyl ether and the resultant solid collected and dried under vacuum, yield of crude material 126 mgs. The peptide was purified by gradient elution on a reverse phase HPLC C18 silica gel column with acetonitrile/water/TFA (0.075%). Fractions containing the pure peptide were concentrated at reduced pressure and lyophilized to afford the product (TFA salts of basic groups) as a fine powder. ES-MS (M+H)$^+$ 891.8 (calc. 891.50).

5.2 Synthesis of Compound 93 (Ac(Chg)R(Tic)(3'-Carbazolyl Ala)) (SEQ ID NO.: 93)

The peptide analog was synthesized on Knorr amide resin (0.1 mmol) utilizing 5 equivalents of N-Fmoc amino acid with HBTU (5 equivalents) in 0.4M N-methyl morpholine in DMF as activator. Coupling reactions were carried out for 1 h at RT, and repeated with 5 equivalents HBTU/N-Fmoc amino acid as required (double coupling). Fmoc removal was accomplished by treatment with 20% piperidine in DMF (2×20 min cycles), affording a free amino N terminus ready for the next amino acid coupling. Final N terminal acylation of the peptide sequence was carried out after Fmoc removal by treatment with the appropriate acid anhydride (acetic anhydride in example 23) in a 0.4 M solution of N-methyl morpholine in DMF (20 min). Upon completion of synthesis the resin was washed sequentially with DMF; ethanol and dichloromethane and dried under vacuum. Peptide analog was cleaved from the resin by treatment with a mixture of TFA (8.8 mL): tri-isopropyl silane (0.5 mL): dichloromethane (0.5 mL): water (0.5 mL) for 45 minutes. The mixture was filtered, the resin washed with TFA (10 mL) and the combined filtrate evaporated under reduced pressure. Trituration with anhydrous diethyl ether afforded the crude peptide as a solid. Peptides were purified to homogeneity by gradient elution on a reverse phase HPLC C18 silica gel column with acetonitrile/water/TFA (0.075%). Fractions containing the pure peptide were concentrated at reduced pressure and lyophilized to afford the peptide (TFA salts of basic groups) as fine powders. ES-MS $(M+H)^+$ 849.8 (calc. 849.47).

5.3 Synthesis of Compound 105 (Ac(Cpg)NHNH [COCH$_2$CH(Ph)CO](4'-Indolyl Ala))K (SEQ ID NO.: 105)

(NH$_2$-(4'-Indolylalanine {N'-Boc})-Lys(N'-Boc)-NH$_2$ was prepared by Fmoc synthesis protocols on Sieber amide resin and cleavage with 1% TFA in dichloromethane (Boc side chain protection remained intact under these conditions). The protected peptide was purified by gradient elution on a reverse phase HPLC C18 silica gel column with acetonitrile/water/TFA (0.075%). Fractions containing the pure peptide were concentrated at reduced pressure and lyophilized to afford the peptide (TFA salts of basic groups) as a fine powder.

To a stirred solution of 3-[N'-(Acetylamino-cyclopentyl-acetyl)-hydrazinocarbonyl]-2-benzyl-propionic acid (35 mgs, 0.09 mmol) in dry THF (0.5 mL) and DMF (0.5 mL) at 0° C. was added N methyl morpholine (12 µL, 0.11 mmol) followed by isobutyl chloroformate (13 µL, 0.1 mmol). Reaction was stirred at 0° C. for 30 min, and a solution of NH$_2$-(4'-Indolylalanine {N'-Boc})-Lys(N'-Boc)-NH$_2$ (44.2 mgs, 0.1 mmol) in dry THF (0.5 mL) and DMF (0.5 mL) was added in one portion. Reaction was allowed to attain RT and stirred for 12 h. The reaction mixture was concentrated at reduced pressure and the residue combined with TFA/ dichloromethane/tri-isopropylsilane/water (2 mL of a 5:4:0.5:0.5 mixture) at RT for 20 min to effect global deprotection of the crude product. The solvent was removed at reduced pressure, diluted with dichloromethane (20 mL) and concentrated. This was repeated two more times to remove all the TFA, and the residue dried under vacuum. The residue was triturated with dry diethyl ether and the resultant solid collected and dried under vacuum, yield of crude material 34 mgs. The peptide was purified by gradient elution on a reverse phase HPLC C18 silica gel column with acetonitrile/water/TFA (0.075%). Fractions containing the pure peptide were concentrated at reduced pressure and lyophilized to afford the product (TFA salts of basic groups) as a fine powder. ES-MS $(M+H)^+$ 704.0 (calc. 703.39).

5.4. HLA II Binding Assay

EBV homozygous cell lines are used as sources of human HLA class II molecules. HLA-DR molecules are purified by affinity chromatography using the monomorphic mAb L243 (American Type Culture Collection, Manassas, Va.) coupled to protein A-Sepharose CL 4B gel (Amersham Pharmacia Biotech). The supernatant from lysed cells after centrifugation (100,000 g for 1 h) is applied to Sepharose 4B and protein A-Sepharose 4B columns and then to the specific antibody column. HLA DR molecules are eluted with 1.1 mM n-dodecyl β-D-maltoside, 500 mM NaCl and 500 mM Na$_2$CO$_3$ (pH 11.5). Fractions are immediately neutralized to pH 7 with 2 mM Tris-HCl (pH 6.8) and extensively dialyzed against 1 mM n-dodecyl β-D-maltoside, 150 mM NaCl, 10 mM phosphate (pH 7) buffer.

HLA-DR molecules are diluted in 10 mM phosphate, 150 mM NaCl, 1 mM n-dodecyl β-D-maltoside, 10 mM citrate, 0.003% thimerosal buffer with a biotinylated reference compound (biotinyl 6-aminocaproic-EAEQLRAYLDGTGVE (SEQ ID NO.: 107) for DRB1*1501 MHC class II molecules) and serial dilutions of competitor peptides and/or compounds of the invention. Samples (100 µl per well) are incubated in 96-wells polypropylene plates at 37° C. for 24 h to 72 h. After neutralization with 50 µl of 450 mM Tris HCl pH 7.5, 0.003% thimerosal, 0.3% BSA, 1 mM n-dodecyl β-D-maltoside buffer, samples are applied to 96-well maxisorp ELISA plates previously coated with 10 mg/ml L243 Mab and saturated with 100 mM Tris HCl pH=7.5, 0.3% BSA, and 0.003% thimerosal buffer. Samples are allowed to bind to the antibody-coated plates for 2 h at room temperature. Bound biotinylated compound is detected by incubating streptavidin-alkaline phosphatase conjugate, and after washings, by the addition of 4-methylumbelliferyl phosphate substrate. Emitted fluorescence is measured at 450 nm upon excitation at 365 nm on a Fluorolite 1000 fluorimeter. Maximal binding is determined by incubating the biotinylated peptide with the MHC class II molecule in the absence of competitor. Binding specificity is assessed by adding an excess of non-biotinylated peptide. Background does not significantly differ from that obtained by incubating the biotinylated peptide without MHC II molecules. Data are expressed as the peptide concentration that prevents binding of 50% of the labeled peptide ($IC_{50}$).

Several compounds of the invention were assayed using the above protocol to demonstrate their selectivity for particular DR molecules as set forth in Table 4, below.

TABLE 4

| Compound | SEQ ID NO | Inhibition of peptide binding $IC_{50}$ nM | | | |
|---|---|---|---|---|---|
| | | DR2b | DR2a | DR1 | DR13 |
| ENPVVHFFKNIV | 1 | 70 | — | — | — |
| AcVHFFKNI | 2 | 450 | — | — | — |
| AcVVHFFKNI | 11 | 9 | 3039 | 1032 | >100,000 |
| AcVRF(1-Nal)KNI | 17 | 70 | 902 | 1673 | >100,000 |
| Ac(Cpg)RFFKNI | 25 | 25 | 630 | 271 | >100,000 |
| Ac(Cpg)R(Tic)FKNI | 33 | 2.5 | 145 | 79 | >100,000 |
| Ac(Chg)RF(4'-IndolylAla)KNI | 79 | 6 | 3581 | 819 | >100,000 |
| Ac(Cpg)R(Tic)F(hPro) | 94 | 75 | >100,000 | >100,000 | >100,000 |
| Ac(Idg)RFFKNI | 64 | 90 | 17 | 52 | >100,000 |
| AcV(Chg)RFFK | 85 | 3 | 685 | 5013 | >100,000 |

5.5. T-Cell Proliferation Inhibition Assay

The compounds of the present invention can be tested for inhibition of T-cell response. One skilled in the art would be familiar with many of the known techniques used to measure T-cell proliferation. See Bolin, D., (2000) J. Med. Chem. 43:2135-2148; Chirathaworn, C. (2002) J. Immunol. 168 (11):5530-5537; Falcioni, F., et. al. (1999) Nature Biotechnology 17:562-567.

Mitomycin C—treated (150 g/ml, 37° C., 60 min.) APCs are preincubated with a stimulatory concentration of a compound of the invention in 96-well U bottom plates (4×10$^4$ LBL or 10$^5$ DR-transgenic spleen cells/well) at 37° C. for 2 h. T cells (2×10$^4$/well) are then added and the cells are cultured for 3 days. Proliferative T-cell response is measured by [$^3$H] thymidine incorporation, using a liquid scintillation counter.

For compound screening, HEL-specific polyclonal T-cell lines and OVA-specific T-cell hybridomas are derived from HLA-DR4-IE chimeric, transgenic mice, and splenocytes of the same transgenic mice serve as APCs. Bolin, D. Id. T-cell inhibitory potency can be measured relative to the $IC_{50}$ of a model peptide or of a compound with known inhibitory activity. Alternatively, standard control compounds identified in the art can be used, e.g., phorbol (10 nM) in combination with ionomycin (0.5 μM).

5.6. Cathepsin Stability Assay

The myelin basic protein-related reference peptide ($AcVRFFKNI-NH_2$) (SEQ ID NO.: 108) is incubated with a buffered solution comprising cathepsin B, D, or L at about 37° C. at pH 6. Degradation products are resolved using reverse phase HPLC (acetonitrile/water/TFA gradient elution). The height of the parent peak is followed as a function of incubation time with the enzyme and plotted relative to an internal standard peak height. The mass of selected peaks is determined to identify cleavage sites.

While the invention has been described with respect to the particular non-limiting embodiments, it will be apparent to those skilled in the art that various changes and modifications can be made without departing from the spirit and scope of the invention as defined in the claims. Such modifications are also intended to fall within the scope of the appended claims.

What we claim is:

1. The compound of Formula II:

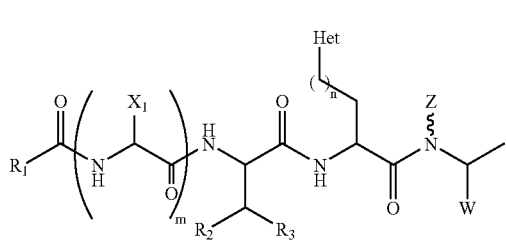

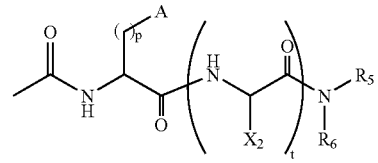

or a pharmaceutically acceptable salt thereof, wherein:
$R_1$ is linear or branched alkyl, alkoxy, alkoxyalkyl, aminoalkyl, alkylaminoalkyl, or dialkylaminoalkyl;

$X_1$ is linear or branched alkyl, hydroxyalkyl, or alkoxyalkyl;

$X_2$ is linear or branched alkyl, heteroalkyl, alkoxycarbonyl, or aminoalkyl;

$R_2$ and $R_3$ are independently hydrogen, or linear or branched alkyl, or $R_2$ and $R_3$ taken together form a substituted or unsubstituted 5-7 membered carbocyclic ring, or $R_2$ and $R_3$ taken together form a substituted or unsubstituted bicyclic ring;

Het is heteroalkyl, aminoalkyl, alkylamido, or a substituted or unsubstituted heterocyclic ring;

$R_5$ and $R_6$ are independently hydrogen, linear or branched alkyl, or $R_5$ and $R_6$ taken together form a substituted or unsubstituted 5-7 membered heterocyclic ring Z is linear or branched alkyl; or Z taken together with W can form a substituted or unsubstituted 6-7 membered heterocyclic ring, W is linear or branched alkyl, substituted or unsubstituted aryl or substituted or unsubstituted arylalky when Z is a linear or branked alkyl;

A is substituted or unsubstituted 5-7 membered heteroaryl ring, a substituted or unsubstituted aryl ring, a substituted or unsubstituted 9-14 membered bicyclic ring; or a substituted or unsubstituted 13-17 membered tricyclic ring;

m is an integer selected from 0 and 1;

n is an integer selected from 0 and 1;

t is an integer selected from 0, 1 and 2;

p is an integer selected from 0 and 1; and wherein the compounds of formula II contain 0, 1, 2 or 3 residues in the D configuration and the remaining residues are in the L configuration.

2. A pharmaceutical composition comprising a compound of claim 1 and a pharmaceutically acceptable carrier.

3. A single unit dosage form comprising a compound of claim 1.

4. The single unit dosage form of claim 3, which is suitable for oral or mucosal administration.

5. The single unit dosage form of claim 3, which is suitable for parenteral administration.

6. The single unit dosage form of claim 3, which is in the form of a tablet, caplet or capsule.

7. The single unit dosage form of claim 3, which is in the form of a solution or suspension.

8. The compound of claim 1, wherein Het is heteroalkyl.

9. The compound of claim 8, wherein the heteroalkyl is alkyl substituted with a guanidino or amidino group.

10. The compound of claim 1, wherein 0, 1, 2 or 3 of the residues has an R configuration.

* * * * *

SEQUENCE LISTING

```
<160> NUMBER OF SEQ ID NOS: 109

<210> SEQ ID NO 1
<211> LENGTH: 11
<212> TYPE: PRT
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II

<400> SEQUENCE: 1

Glu Asn Pro Val Val His Phe Phe Lys Asn Ile
 1               5                  10

<210> SEQ ID NO 2
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 2

Val His Phe Phe Lys Asn Ile
 1               5

<210> SEQ ID NO 3
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 3

Ile His Phe Phe Lys Asn Ile
 1               5

<210> SEQ ID NO 4
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
```

```
<400> SEQUENCE: 4

Val Arg Phe Phe Lys Asn Ile
1               5

<210> SEQ ID NO 5
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 5

Val His Pro Phe Lys Asn Ile
1               5

<210> SEQ ID NO 6
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 6

Val His Phe Phe Pro Asn Ile
1               5

<210> SEQ ID NO 7
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 7

Val His Phe Phe Lys Thr Ile
1               5

<210> SEQ ID NO 8
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 8

Val Arg Phe Ala Asn Ile
1               5

<210> SEQ ID NO 9
<211> LENGTH: 5
<212> TYPE: PRT
<213> ORGANISM: Artificial Sequence
```

```
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 9

Val Arg Pro Phe Ser
 1               5

<210> SEQ ID NO 10
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 10

Val Arg Leu Phe Ala Asn Ile
 1               5

<210> SEQ ID NO 11
<211> LENGTH: 8
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 11

Val Val His Phe Phe Lys Asn Ile
 1               5

<210> SEQ ID NO 12
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 12

Val Thr Phe Phe Lys Asn Ile
 1               5

<210> SEQ ID NO 13
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 3
<223> OTHER INFORMATION: Xaa = N-Me Ala
```

```
<400> SEQUENCE: 13

Val His Xaa Phe Lys Asn Ile
1               5

<210> SEQ ID NO 14
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4,6
<223> OTHER INFORMATION: Xaa = N-Me Ala

<400> SEQUENCE: 14

Val His Ala Xaa Phe Xaa Asn
1               5

<210> SEQ ID NO 15
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 15

Val His Phe Val Lys Asn Ile
1               5

<210> SEQ ID NO 16
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 2-Nal

<400> SEQUENCE: 16

Val Arg Phe Xaa Lys Asn Ile
1               5

<210> SEQ ID NO 17
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 2-Nal
```

```
<400> SEQUENCE: 17

Val Arg Phe Xaa Lys Asn Ile
1               5

<210> SEQ ID NO 18
<211> LENGTH: 8
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 6
<223> OTHER INFORMATION: Xaa = N-Me Ala

<400> SEQUENCE: 18

Val His Phe Phe Ala Xaa Asn Ile
1               5

<210> SEQ ID NO 19
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 19

Val Arg Leu Phe Lys Asn
1               5

<210> SEQ ID NO 20
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 4'-Pyridyl Ala

<400> SEQUENCE: 20

Val Arg Phe Xaa Lys Asn Ile
1               5

<210> SEQ ID NO 21
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 21
```

Val Arg Ala Phe Ala Asn
1               5

<210> SEQ ID NO 22
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = O-Benzyl Ser

<400> SEQUENCE: 22

Val Arg Ala Xaa Lys Asn Ile
1               5

<210> SEQ ID NO 23
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Tic

<400> SEQUENCE: 23

Xaa Phe Lys Asn Ile
1               5

<210> SEQ ID NO 24
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 3
<223> OTHER INFORMATION: Xaa = Tic

<400> SEQUENCE: 24

Val Arg Xaa Phe Lys Asn Ile
1               5

<210> SEQ ID NO 25
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN

```
<222> LOCATION: 1
<223> OTHER INFORMATION: Xaa = Cpg

<400> SEQUENCE: 25

Xaa Arg Phe Phe Lys Asn Ile
 1               5

<210> SEQ ID NO 26
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 26

Val His Ser Phe Ser Asn
 1               5

<210> SEQ ID NO 27
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 3' Cyano Phe

<400> SEQUENCE: 27

Val Arg Phe Xaa Lys Asn Ile
 1               5

<210> SEQ ID NO 28
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 3
<223> OTHER INFORMATION: Xaa = Tiq

<400> SEQUENCE: 28

Val Arg Xaa Phe Lys Asn Ile
 1               5

<210> SEQ ID NO 29
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
```

```
<221> NAME/KEY: MUTAGEN
<222> LOCATION: 1
<223> OTHER INFORMATION: Xaa = Tiq

<400> SEQUENCE: 29

Xaa Phe Lys Asn Ile
 1               5

<210> SEQ ID NO 30
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE:

```
<220> FEATURE:
<221> NAME/KEY: MUTAGEN
<222> LOCATION: 1
<223> OTHER INFORMATION: Xaa = Cpg
<220> FEATURE:
<221> NAME/KEY: MUTAGEN
<222> LOCATION: 3
<223> OTHER INFORMATION: Xaa = Tic

<400> SEQUENCE: 33

Xaa Arg Xaa Phe Lys Asn Ile
1               5

<210> SEQ ID NO 34
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 3
<223> OTHER INFORMATION: Xaa = homo Pro

<400> SEQUENCE: 34

Val Arg Xaa Phe Lys Asn Ile
1               5

<210> SEQ ID NO 35
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 35

Val Arg Phe Phe Lys
1               5

<210> SEQ ID NO 36
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 36

Val Lys Phe Phe Lys Asn Ile
1               5

<210> SEQ ID NO 37
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
```

```
            to MHC class II
<220> FEATURE:
<221> NAME/KEY: MOD_RES
<222> LOCATION: 2
<223> OTHER INFORMATION: Xaa = Orn

<400> SEQUENCE: 37

Val Xaa Phe Phe Lys Asn Ile
 1               5

<210> SEQ ID NO 38
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = N' Alloc Dab

<400> SEQUENCE: 38

Val Xaa Phe Phe Lys Asn Ile
 1               5

<210> SEQ ID NO 39
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Cha

<400> SEQUENCE: 39

Xaa Arg Phe Phe Lys Asn Ile
 1               5

<210> SEQ ID NO 40
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = 2' Furanyl Ala

<400> SEQUENCE: 40

Xaa Arg Phe Phe Lys Asn Ile
 1               5

<210> SEQ ID NO 41
<211> LENGTH: 7
<212> TYPE: PRT
<213> ORGANISM: Artificial Sequence
```

```
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = 2' Thienyl Ala

<400> SEQUENCE: 41

Xaa Arg Phe Phe Lys Asn Ile
 1               5

<210> SEQ ID NO 42
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = 2' Furanyl Ala

<400> SEQUENCE: 42

Val Arg Xaa Phe Lys Asn Ile
 1               5

<210> SEQ ID NO 43
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 3
<223> OTHER INFORMATION: Xaa = 2' Thienyl Ala

<400> SEQUENCE: 43

Val Arg Xaa Phe Lys Asn Ile
 1               5

<210> SEQ ID NO 44
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 44

Val Arg Ala Phe Lys Asn Ile
 1               5

<210> SEQ ID NO 45
<211> LENGTH: 5
<212> TYPE: PRT
```

-continued

```
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Benzoyl-Val

<400> SEQUENCE: 45

Xaa Arg Phe Phe Lys
 1              5

<210> SEQ ID NO 46
<211> LENGTH: 5
<212> TYPE: PRT
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Isobutanoyl-Val

<400> SEQUENCE: 46

Xaa Arg Phe Phe Lys
 1              5

<210> SEQ ID NO 47
<211> LENGTH: 5
<212> TYPE: PRT
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Butanoyl-Val

<400> SEQUENCE: 47

Xaa Arg Phe Phe Lys
 1              5

<210> SEQ ID NO 48
<211> LENGTH: 5
<212> TYPE: PRT
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = IsoValeroyl-Val

<400> SEQUENCE: 48

Xaa Arg Phe Phe Lys
 1              5

<210> SEQ ID NO 49
<211> LENGTH: 5
<212> TYPE: PRT
<213> ORGANISM: Artificial Sequence
<220> FEATURE:
<221> NAME/KEY: ACETYLATION
```

```
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1,3,5
<223> OTHER INFORMATION: Xaa = Cpg, Tic, Homo Pro

<400> SEQUENCE: 49

Xaa Arg Xaa Phe Xaa
 1               5

<210> SEQ ID NO 50
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 50

Val Val Arg Phe Phe
 1               5

<210> SEQ ID NO 51
<211> LENGTH: 5
<212> TYPE: PRT
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = 3-(Imadazoyl-4-yl)propionyl - Val

<400> SEQUENCE: 51

Xaa Arg Phe Phe Lys
 1               5

<210> SEQ ID NO 52
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Chg

<400> SEQUENCE: 52

Xaa Arg Phe Phe Lys Asn Ile
 1               5

<210> SEQ ID NO 53
<211> LENGTH: 7
<212> TYPE: PRT
<213> ORGANISM: Artificial Sequence
<220> FEATURE:
<221> NAME/KEY: ACETYLATION
<222> LOCATION: 1
```

```
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 5
<223> OTHER INFORMATION: Xaa = Dap

<400> SEQUENCE: 53

Val Arg Phe Phe Xaa Asn Ile
 1               5

<210> SEQ ID NO 54
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = Dab

<400> SEQUENCE: 54

Val Xaa Phe Phe Lys Asn Ile
 1               5

<210> SEQ ID NO 55
<211> LENGTH: 8
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 55

Val Val Ala Gly Phe Lys Asn Ile
 1               5

<210> SEQ ID NO 56
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 56

Val Ala Gly Phe Lys Asn Ile
 1               5

<210> SEQ ID NO 57
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
```

-continued

```
<220> FEATURE:
<221> NAME/KEY: MUTAGEN
<222> LOCATION: 2
<223> OTHER INFORMATION: Xaa = Dap

<400> SEQUENCE: 57

Val Xaa Phe Phe Lys Asn Ile
 1               5

<210> SEQ ID NO 58
<211> LENGTH: 4
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 58

Val Arg Phe Phe
 1

<210> SEQ ID NO 59
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 3' phenoxy Phe

<400> SEQUENCE: 59

Val Arg Phe Xaa Lys Asn Ile
 1               5

<210> SEQ ID NO 60
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 5
<223> OTHER INFORMATION: Xaa = 3' Methylamino Phe

<400> SEQUENCE: 60

Val Val Lys Phe Xaa Lys
 1               5

<210> SEQ ID NO 61
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
``` to MHC class II

<400> SEQUENCE: 61

Phe Arg Phe Phe Lys Asn Ile
 1               5

<210> SEQ ID NO 62
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 6
<223> OTHER INFORMATION: Xaa = Beta Ala

<400> SEQUENCE: 62

Val Arg Phe Phe Lys Xaa Ile
 1               5

<210> SEQ ID NO 63
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = (3'-amino-1'-carboxymethyl-pyridin-
      2'-one)-Phe

<400> SEQUENCE: 63

Val Xaa Lys Asn Ile
 1               5

<210> SEQ ID NO 64
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Idg

<400> SEQUENCE: 64

Xaa Arg Phe Phe Lys Asn Ile
 1               5

<210> SEQ ID NO 65
<211> LENGTH: 6
<212> TYPE: PRT
<213> ORGANISM: Artificial Sequence
<220> FEATURE:
<221> NAME/KEY: ACETYLATION
<222> LOCATION: 1

```
<223> OTHER INFORMATION: Novel compounds of formula I or a
      pharmaceutically acceptable salt which inhibiting antigen binding
      to MHC class II

<400> SEQUENCE: 65

Ala Val Arg Phe Phe Lys
 1               5

<210> SEQ ID NO 66
<211> LENGTH: 8
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 66

Ala Val His Phe Phe Lys Asn Ile
 1               5

<210> SEQ ID NO 67
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = 2' Furanyl Ala

<400> SEQUENCE: 67

Val Xaa Phe Phe Lys Asn Ile
 1               5

<210> SEQ ID NO 68
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = 2' Thienyl Ala

<400> SEQUENCE: 68

Val Xaa Phe Phe Lys Asn Ile
 1               5

<210> SEQ ID NO 69
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
```

```
<220> FEATURE:
<221> NAME/KEY: MUTAGEN
<222> LOCATION: 5
<223> OTHER INFORMATION: Xaa = 3' Cyano Phe

<400> SEQUENCE: 69

Val Val Lys Phe Xaa Lys
1               5

<210> SEQ ID NO 70
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: ACETYLATION
<222> LOCATION: 1
<223> OTHER INFORMATION: Xaa = Phg

<400> SEQUENCE: 70

Xaa Arg Phe Phe Lys Asn Ile
1               5

<210> SEQ ID NO 71
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 3, 5
<223> OTHER INFORMATION: Xaa = Tic, homo Pro

<400> SEQUENCE: 71

Ile Arg Xaa Phe Xaa
1               5

<210> SEQ ID NO 72
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 72

Leu Arg Phe Phe Lys Asn Ile
1               5

<210> SEQ ID NO 73
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
```

```
        to MHC class II
<220> FEATURE:
<221> NAME/KEY: MUTAGEN
<222> LOCATION: 3
<223> OTHER INFORMATION: Xaa = Phg

<400> SEQUENCE: 73

Val Arg Xaa Phe Lys Asn Ile
1               5

<210> SEQ ID NO 74
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
        pharmaceutically acceptable salt which inhibiting antigen binding
        to MHC class II
<220> FEATURE:
<221> NAME/KEY: MUTAGEN
<222> LOCATION: 5
<223> OTHER INFORMATION: Xaa = 3' phenoxy Phe

<400> SEQUENCE: 74

Val Val Arg Phe Xaa Lys
1               5

<210> SEQ ID NO 75
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
        pharmaceutically acceptable salt which inhibiting antigen binding
        to MHC class II
<220> FEATURE:
<221> NAME/KEY: MUTAGEN
<222> LOCATION: 4
<223> OTHER INFORMATION: Xaa = Phg

<400> SEQUENCE: 75

Val Arg Phe Xaa Lys Asn Ile
1               5

<210> SEQ ID NO 76
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
        pharmaceutically acceptable salt which inhibiting antigen binding
        to MHC class II
<220> FEATURE:
<221> NAME/KEY: MUTAGEN
<222> LOCATION: 6
<223> OTHER INFORMATION: Xaa = beta Ala

<400> SEQUENCE: 76

Val Arg Phe Phe Lys Xaa
1               5

<210> SEQ ID NO 77
<211> LENGTH: 7
<212> TYPE: PRT
<213> ORGANISM: Artificial Sequence
```

```
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 7
<223> OTHER INFORMATION: Xaa = beta Ala

<400> SEQUENCE: 77

Val Val Arg Phe Phe Lys Xaa
 1               5

<210> SEQ ID NO 78
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Chg

<400> SEQUENCE: 78

Xaa Val Arg Phe Phe Lys
 1               5

<210> SEQ ID NO 79
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Chg
<220> FEATURE:
<221> NAME/KEY: MUTAGEN
<222> LOCATION: 4
<223> OTHER INFORMATION: Xaa = 4'-Indolyl Ala

<400> SEQUENCE: 79

Xaa Arg Phe Xaa Lys Asn Ile
 1               5

<210> SEQ ID NO 80
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 3'-Carbazolyl Ala

<400> SEQUENCE: 80
```

```
Val Arg Phe Xaa Lys Asn Ile
 1               5

<210> SEQ ID NO 81
<211> LENGTH: 4
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = Cpg
<220> FEATURE:
<221> NAME/KEY: MUTAGEN
<222> LOCATION: 2
<223> OTHER INFORMATION: Xaa = NHNH(COCH2CH(Ph)CO)Lys

<400> SEQUENCE: 81

Xaa Xaa Asn Ile
 1

<210> SEQ ID NO 82
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 3'-amino Phe

<400> SEQUENCE: 82

Val Arg Phe Xaa Lys Asn Ile
 1               5

<210> SEQ ID NO 83
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 83

Trp Arg Phe Phe Lys Asn Ile
 1               5

<210> SEQ ID NO 84
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
```

-continued

```
<221> NAME/KEY: MUTAGEN
<222> LOCATION: 2
<223> OTHER INFORMATION: Xaa = (omiga, omiga -dimethyl) Lys

<400> SEQUENCE: 84

Val Xaa Phe Phe Lys Asn Ile
 1               5

<210> SEQ ID NO 85
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = Chg

<400> SEQUENCE: 85

Val Xaa Arg Phe Phe Lys
 1               5

<210> SEQ ID NO 86
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = nor Arg

<400> SEQUENCE: 86

Val Xaa Phe Phe Lys Asn Ile
 1               5

<210> SEQ ID NO 87
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 4
<223> OTHER INFORMATION: Xaa = 3-Acetylamino Phe

<400> SEQUENCE: 87

Val Arg Phe Xaa Lys Asn Ile
 1               5

<210> SEQ ID NO 88
<211> LENGTH: 5
<212> TYPE: PRT
<213> ORGANISM: Artificial Sequence
<220> FEATURE:
<221> NAME/KEY: ACETYLATION
```

-continued

```
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1,3,5
<223> OTHER INFORMATION: Xaa = Chg, Tic. 4Hyp

<400> SEQUENCE: 88

Xaa Arg Xaa Phe Xaa
 1               5

<210> SEQ ID NO 89
<211> LENGTH: 3
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1,3
<223> OTHER INFORMATION: Xaa = Chg, Tic

<400> SEQUENCE: 89

Xaa Arg Xaa
 1

<210> SEQ ID NO 90
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 90

Val Lys Phe Phe Glu Asn Ile
 1               5

<210> SEQ ID NO 91
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II

<400> SEQUENCE: 91

Val Arg Ile Phe Lys Asn Ile
 1               5

<210> SEQ ID NO 92
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
```

-continued

```
      to MHC class II
<220> FEATURE:
<221> NAME/KEY: MUTAGEN
<222> LOCATION: 1,2
<223> OTHER INFORMATION: Xaa = Cpg, NHNH(COCH2CH(Ph)CO)Phe

<400> SEQUENCE: 92

Xaa Xaa Lys Asn Ile
 1               5

<210> SEQ ID NO 93
<211> LENGTH: 4
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1, 3, 4
<223> OTHER INFORMATION: Xaa = Chg, Tic, 3'-Carbazolyl Ala

<400> SEQUENCE: 93

Xaa Arg Xaa Xaa
 1

<210> SEQ ID NO 94
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1,3,5
<223> OTHER INFORMATION: Xaa = Chg, Tic, homo Pro

<400> SEQUENCE: 94

Xaa Arg Xaa Phe Xaa
 1               5

<210> SEQ ID NO 95
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1,3
<223> OTHER INFORMATION: Xaa = Idg. Tic

<400> SEQUENCE: 95

Xaa Arg Xaa Phe Lys
 1               5

<210> SEQ ID NO 96
<211> LENGTH: 6
<212> TYPE: PRT
<213> ORGANISM: Artificial Sequence

```
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: ACETYLATION
<222> LOCATION: 2
<223> OTHER INFORMATION: Xaa = Idg
<220> FEATURE:
<221> NAME/KEY: ACETYLATION
<222> LOCATION: 4
<223> OTHER INFORMATION: Xaa = Tic

<400> SEQUENCE: 96

Val Xaa Arg Xaa Phe Lys
 1               5

<210> SEQ ID NO 97
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = Chg
<220> FEATURE:
<221> NAME/KEY: MUTAGEN
<222> LOCATION: 4
<223> OTHER INFORMATION: Xaa = Tic

<400> SEQUENCE: 97

Val Xaa Arg Xaa Phe
 1               5

<210> SEQ ID NO 98
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = Chg

<400> SEQUENCE: 98

Val Xaa Arg Phe Phe Lys
 1               5

<210> SEQ ID NO 99
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
```

```
<222> LOCATION: 1
<223> OTHER INFORMATION: Xaa = Chg
<220> FEATURE:
<221> NAME/KEY: MUTAGEN
<222> LOCATION: 3
<223> OTHER INFORMATION: Xaa = Tic
<220> FEATURE:
<221> NAME/KEY: MUTAGEN
<222> LOCATION: 4
<223> OTHER INFORMATION: Xaa = 3'-Carbazolyl Ala

<400> SEQUENCE: 99

Xaa Arg Xaa Xaa Gly
 1               5

<210> SEQ ID NO 100
<211> LENGTH: 6
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = Chg
<220> FEATURE:
<221> NAME/KEY: MUTAGEN
<222> LOCATION: 4
<223> OTHER INFORMATION: Xaa = Tic
<220> FEATURE:
<221> NAME/KEY: MUTAGEN
<222> LOCATION: 5
<223> OTHER INFORMATION: Xaa = 3'-Carbazolyl Ala

<400> SEQUENCE: 100

Val Xaa Arg Xaa Xaa Gly
 1               5

<210> SEQ ID NO 101
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 5
<223> OTHER INFORMATION: Xaa = 3'-Acetylaminomethyl Phe

<400> SEQUENCE: 101

Val Val Arg Phe Xaa
 1               5

<210> SEQ ID NO 102
<211> LENGTH: 5
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
```

```
<222> LOCATION: 5
<223> OTHER INFORMATION: Xaa = 3'-Methylsulphonyl aminomethyl Phe

<400> SEQUENCE: 102

Val Val Arg Phe Xaa
 1               5

<210> SEQ ID NO 103
<211> LENGTH: 5
<212> TYPE: PRT
<213> ORGANISM: Artificial Sequence
<220> FEATURE:
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1
<223> OTHER INFORMATION: Xaa = (2,6-Dimethyl Benzoyl)-Val

<400> SEQUENCE: 103

Val Arg Phe Phe Lys
 1               5

<210> SEQ ID NO 104
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 2
<223> OTHER INFORMATION: Xaa = homo Arg

<400> SEQUENCE: 104

Val Xaa Phe Phe Lys Asn Ile
 1               5

<210> SEQ ID NO 105
<211> LENGTH: 3
<212> TYPE: PRT
<213> ORGANISM: Artificial Sequence
<220> FEATURE:
<221> NAME/KEY: ACETYLATION
<222> LOCATION: 1
<223> OTHER INFORMATION: Novel compounds of formula I or a
      pharmaceutically acceptable salt which inhibiting antigen binding
      to MHC class II
<220> FEATURE:
<221> NAME/KEY: MUTAGEN
<222> LOCATION: 1,2
<223> OTHER INFORMATION: Xaa = Cpg, NHNH(COCH2CH(Ph)CO)-(4'-Indolyl Ala)

<400> SEQUENCE: 105

Xaa Xaa Lys
 1

<210> SEQ ID NO 106
<211> LENGTH: 11
<212> TYPE: PRT
<213> ORGANISM: Artificial Sequence
<220> FEATURE:
<223> OTHER INFORMATION: partially stabilized peptide developed by
      Cytel, Inc.
<220> FEATURE:
<221> NAME/KEY: MOD_RES
```

```
<222> LOCATION: 1, 2, 11
<223> OTHER INFORMATION: Xaa = Cha, d-Ala, d-Ala

<400> SEQUENCE: 106

Xaa Xaa Ala Ala Ala Lys Thr Ala Ala Ala Xaa
 1               5                  10

<210> SEQ ID NO 107
<211> LENGTH: 15
<212> TYPE: PRT
<213> ORGANISM: Artificial Sequence
<220> FEATURE:
<223> OTHER INFORMATION: biotinylated reference compound
<220> FEATURE:
<221> NAME/KEY: MUTAGEN
<222> LOCATION: 1
<223> OTHER INFORMATION: Xaa = biotinyl 6-aminocaproic-Glu

<400> SEQUENCE: 107

Xaa Ala Glu Gln Leu Arg Ala Tyr Leu Asp Gly Thr Gly Val Glu
 1               5                  10                  15

<210> SEQ ID NO 108
<211> LENGTH: 7
<212> TYPE: PRT
<213> ORGANISM: Artificial Sequence
<220> FEATURE:
<221> NAME/KEY: ACETYLATION
<222> LOCATION: 1
<223> OTHER INFORMATION: myelin basic protein-related reference peptide

<400> SEQUENCE: 108

Val Arg Phe Phe Lys Asn Ile
 1               5

<210> SEQ ID NO 109
<211> LENGTH: 4
<212> TYPE: PRT
<213> ORGANISM: Artificial Sequence
<220> FEATURE:
<223> OTHER INFORMATION: synthetic compound used for the synthesis of
      Compound 92
<220> FEATURE:
<221> NAME/KEY: MOD_RES
<222> LOCATION: 2
<223> OTHER INFORMATION: modified by adding N'-Boc side chain
<220> FEATURE:
<221> NAME/KEY: MOD_RES
<222> LOCATION: 3
<223> OTHER INFORMATION: modified by adding Trt (trityl) side chain

<400> SEQUENCE: 109

Phe Lys Asn Ile
```